US 6,706,000 B2

United States Patent
Perez et al.

(10) Patent No.: US 6,706,000 B2
(45) Date of Patent: *Mar. 16, 2004

(54) METHODS AND APPARATUS FOR EXPRESSING BODY FLUID FROM AN INCISION

(75) Inventors: Edward P. Perez, Menlo Park, CA (US); Jeffrey N. Roe, San Ramon, CA (US); Charles C. Raney, Scotts Valley, CA (US)

(73) Assignee: Amira Medical, Scotts Valley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/879,991

(22) Filed: Jun. 14, 2001

(65) Prior Publication Data

US 2002/0022789 A1 Feb. 21, 2002

Related U.S. Application Data

(63) Continuation-in-part of application No. 09/542,040, filed on Mar. 31, 2000, now Pat. No. 6,464,649, which is a continuation of application No. 09/285,021, filed on Apr. 1, 1999, now Pat. No. 6,066,103, which is a continuation of application No. 08/975,978, filed on Nov. 21, 1997, now Pat. No. 5,964,718.

(51) Int. Cl.⁷ .................................................. A61B 5/00
(52) U.S. Cl. ........................ 600/583; 600/573; 606/181
(58) Field of Search ................................ 600/573, 576, 600/583; 606/181–183

(56) References Cited

U.S. PATENT DOCUMENTS

| 254,444 A | 2/1882 | Vogel et al. |
| 1,960,889 A | 5/1934 | Benedict |
| 2,594,621 A | 4/1952 | Derrick |

(List continued on next page.)

FOREIGN PATENT DOCUMENTS

| DE | 34 26 090 A1 | 4/1985 |
| DE | 3708031 | 11/1987 |
| EP | 0 212 906 A2 | 4/1987 |

(List continued on next page.)

OTHER PUBLICATIONS

Ash, et al., "A Subcutaneous Capillary Filtrate . . . ", ASAIO Journal, pp. M699–M705 (1993).
Ash et al., "Subcutaneous Capillary Filtrate", ASAIO Journal, pp. M416–M420 (1992).
Brace, et al., "Reevaluation of the needle", American Journal of Physics, vol. 229, pp. 603–607 (1975).
Ginsberg, "An Overview of Minimally", Clinical Chemical, vol. 38, pp. 1596–1600 (1992).
Janle–Swain, et al., "Use of Capillary", Trans America Social Artificial Internal Organs, pp. 336–400 (1987).
Kayashima, et al., "Suction Effusion Fluid From", American Physics Society, pp. H1623–H1626 (1992).

(List continued on next page.)

*Primary Examiner*—Charles Marmor
(74) *Attorney, Agent, or Firm*—Woodard, Emhardt, Moriarty, McNett & Henry LLP

(57) ABSTRACT

A sample of a body fluid such as blood or interstitial fluid is obtained from a body by lancing a portion of a user's skin, preferably in an area other than a finger tip, to form an incision. After the needle has been removed from the incision, a force is applied to depress the skin in a manner forming a ring of depressed body tissue in surrounding relationship to the incision, causing the incision to bulge and the sides of the incision to open, whereby body fluid is forced out through the opening of the incision. A stimulator member is mounted to an end of a lancet-carrying housing for applying the force. The stimulator member can be movable relative to the housing, and can be either heated or vibrated to promote movement of the body fluid.

31 Claims, 16 Drawing Sheets

U.S. PATENT DOCUMENTS

| | | |
|---|---|---|
| 2,646,799 A | 7/1953 | Jacoby, Jr. |
| 3,030,959 A | 4/1962 | Grunert |
| 3,040,744 A | 6/1962 | Hoggard |
| 3,068,868 A | 12/1962 | Skopyk |
| 3,221,739 A | 12/1965 | Rosenthal |
| 3,235,337 A | 2/1966 | Artis |
| 3,358,689 A | 12/1967 | Higgins |
| 3,486,504 A | 12/1969 | Austin |
| 3,623,475 A | 11/1971 | Sanz |
| 3,626,929 A | 12/1971 | Sanz et al. |
| 3,685,509 A | 8/1972 | Bentall |
| 3,734,085 A | 5/1973 | Russell |
| 3,741,197 A | 6/1973 | Sanz et al. |
| 3,774,611 A | 11/1973 | Tussey et al. |
| 3,933,439 A | 1/1976 | McDonald |
| D238,710 S | 2/1976 | Cacanindin |
| 3,964,482 A | 6/1976 | Gerstel et al. |
| 4,151,832 A | 5/1979 | Hamer |
| 4,203,446 A | 5/1980 | Hofert et al. |
| 4,235,234 A | 11/1980 | Whitney et al. |
| 4,360,016 A | 11/1982 | Sarrine |
| 4,368,738 A | 1/1983 | Tersteegen et al. |
| 4,375,815 A | 3/1983 | Burns |
| 4,383,530 A | 5/1983 | Bruno |
| 4,397,643 A | 8/1983 | Rygiel |
| 4,460,354 A | 7/1984 | Weilbacher et al. |
| 4,462,405 A | 7/1984 | Ehrlich |
| 4,469,110 A | 9/1984 | Slama |
| 4,503,856 A | 3/1985 | Cornell et al. |
| 4,517,978 A | 5/1985 | Levin et al. |
| 4,564,513 A | 1/1986 | Becher et al. |
| 4,580,564 A | 4/1986 | Anderson |
| 4,622,974 A | 11/1986 | Coleman et al. |
| 4,627,445 A | 12/1986 | Garcia et al. |
| 4,637,403 A | 1/1987 | Garcia et al. |
| 4,637,978 A | 1/1987 | Dappen |
| 4,648,408 A | 3/1987 | Hutcheson et al. |
| 4,653,511 A | 3/1987 | Goch et al. |
| 4,653,513 A | 3/1987 | Dombrowski |
| 4,654,513 A | 3/1987 | Hennessy |
| 4,658,821 A | 4/1987 | Chiodo et al. |
| 4,660,570 A | 4/1987 | Dombrowski |
| 4,677,979 A | 7/1987 | Burns |
| 4,685,463 A | 8/1987 | Williams |
| 4,687,000 A | 8/1987 | Eisenhardt et al. |
| 4,787,398 A | 11/1988 | Garcia et al. |
| 4,790,979 A | 12/1988 | Terminiello et al. |
| 4,805,623 A | 2/1989 | Jobsis |
| RE32,922 E | 5/1989 | Levin et al. |
| 4,844,095 A | 7/1989 | Chiodo et al. |
| 4,850,973 A | 7/1989 | Jordan et al. |
| 4,858,607 A | 8/1989 | Jordan et al. |
| 4,869,249 A | 9/1989 | Crossman et al. |
| 4,873,993 A | 10/1989 | Meserol et al. |
| 4,883,068 A | 11/1989 | Dechow |
| D305,065 S | 12/1989 | Büchel et al. |
| 4,895,147 A | 1/1990 | Bodicky et al. |
| 4,920,977 A | 5/1990 | Haynes |
| 4,924,879 A | 5/1990 | O'Brien |
| 4,925,447 A | 5/1990 | Rosenblatt |
| 4,953,552 A | 9/1990 | DeMarzo |
| 4,976,724 A | 12/1990 | Nieto et al. |
| 4,981,473 A | 1/1991 | Rosenblatt |
| 4,990,154 A | 2/1991 | Brown et al. |
| 4,994,068 A | 2/1991 | Hufnagle |
| 4,994,073 A | 2/1991 | Green |
| 4,995,402 A | 2/1991 | Smith et al. |
| 5,002,054 A | 3/1991 | Ash et al. |
| 5,014,718 A | 5/1991 | Mitchen |
| 5,019,059 A | 5/1991 | Goldberg et al. |
| 5,029,583 A | 7/1991 | Meserol et al. |
| 5,035,704 A | 7/1991 | Lambert et al. |
| 5,052,403 A | 10/1991 | Haber et al. |
| 5,054,499 A | 10/1991 | Swierczek |
| 5,066,859 A | 11/1991 | Karkar et al. |
| 5,070,884 A | 12/1991 | Columbus et al. |
| 5,070,886 A | 12/1991 | Mitchen et al. |
| D324,423 S | 3/1992 | Ahlstrand et al. |
| 5,102,404 A | 4/1992 | Goldberg et al. |
| 5,163,442 A | 11/1992 | Ono |
| 5,165,418 A | 11/1992 | Tankovich |
| D332,306 S | 1/1993 | Garth et al. |
| 5,193,552 A | 3/1993 | Columbus et al. |
| 5,195,534 A | 3/1993 | Sarrine |
| 5,201,324 A | 4/1993 | Swierczek |
| 5,217,480 A | 6/1993 | Haber et al. |
| 5,231,993 A | 8/1993 | Haber et al. |
| 5,277,198 A | 1/1994 | Kanner et al. |
| 5,279,294 A | 1/1994 | Anderson et al. |
| 5,279,586 A | 1/1994 | Balkwill |
| 5,282,822 A | 2/1994 | Macors et al. |
| 5,304,193 A | 4/1994 | Zhadanov |
| 5,309,924 A | 5/1994 | Peabody |
| 5,318,583 A | 6/1994 | Rabenau et al. |
| 5,318,584 A | 6/1994 | Lange et al. |
| 5,320,607 A | 6/1994 | Ishibashi |
| 5,324,302 A | 6/1994 | Crouse |
| 5,324,303 A | 6/1994 | Strong et al. |
| 5,353,806 A | 10/1994 | Heinzelman et al. |
| 5,366,470 A | 11/1994 | Ramel |
| 5,368,047 A | 11/1994 | Suzuki et al. |
| 5,387,203 A | 2/1995 | Goodrich |
| 5,395,387 A | 3/1995 | Burns |
| 5,402,798 A | 4/1995 | Swierczek et al. |
| 5,421,816 A | 6/1995 | Lipkovker |
| 5,423,758 A | 6/1995 | Shaw |
| 5,423,847 A | 6/1995 | Strong et al. |
| 5,445,611 A | 8/1995 | Eppstein et al. |
| 5,456,875 A | 10/1995 | Lambert |
| 5,458,140 A | 10/1995 | Eppstein et al. |
| 5,487,748 A | 1/1996 | Marshall et al. |
| 5,512,158 A | 4/1996 | Cole |
| 5,518,006 A | 5/1996 | Mawhirt et al. |
| D371,440 S | 7/1996 | Petersen |
| 5,540,709 A | 7/1996 | Ramel |
| 5,545,173 A | 8/1996 | Herbst |
| 5,545,174 A | 8/1996 | Schenk et al. |
| 5,549,584 A | 8/1996 | Gross |
| 5,554,166 A | 9/1996 | Lange et al. |
| 5,569,212 A | 10/1996 | Brown |
| 5,582,184 A | 12/1996 | Erickson et al. |
| D378,612 S | 3/1997 | Clark et al. |
| 5,607,401 A | 3/1997 | Humphrey |
| 5,611,809 A | 3/1997 | Marshall et al. |
| 5,613,978 A | 3/1997 | Harding |
| 5,624,458 A | 4/1997 | Lipscher |
| 5,628,309 A | 5/1997 | Brown |
| 5,628,764 A | 5/1997 | Schraga |
| 5,628,765 A | 5/1997 | Morita |
| 5,638,828 A | 6/1997 | Lauks et al. |
| 5,662,127 A | 9/1997 | De Vaughn |
| 5,666,966 A * | 9/1997 | Horie et al. ................ 600/573 |
| 5,671,753 A | 9/1997 | Pitesky |
| 5,680,872 A | 10/1997 | Sesekura et al. |
| 5,682,233 A | 10/1997 | Brinda |
| 5,700,695 A | 12/1997 | Yassinzadeh et al. |
| 5,707,384 A | 1/1998 | Kim |
| 5,709,699 A | 1/1998 | Warner |
| 5,730,753 A | 3/1998 | Morita |
| 5,741,291 A | 4/1998 | Yoo |
| RE35,803 E | 5/1998 | Lange et al. |

| | | |
|---|---|---|
| 5,746,217 A | 5/1998 | Erickson et al. |
| 5,755,733 A | 5/1998 | Morita |
| 5,788,652 A | 8/1998 | Rahn |
| 5,820,570 A | 10/1998 | Erickson et al. |
| 5,823,973 A | 10/1998 | Racchini et al. |
| 5,857,983 A | 1/1999 | Douglas et al. |
| 5,871,494 A | 2/1999 | Simons et al. |
| 5,873,887 A | 2/1999 | King et al. |
| 5,879,311 A | 3/1999 | Duchon et al. |
| 5,885,219 A | 3/1999 | Nightengale |
| 5,891,053 A | 4/1999 | Sesekura |
| 5,916,222 A | 6/1999 | Iwasaki et al. |
| 5,916,230 A | 6/1999 | Brenneman et al. |
| 5,947,957 A | 9/1999 | Morris |
| 5,951,492 A | 9/1999 | Douglas et al. |
| 5,951,493 A * | 9/1999 | Douglas et al. ............. 600/583 |
| 5,964,718 A * | 10/1999 | Duchon et al. ............. 600/583 |
| 5,971,941 A | 10/1999 | Simons et al. |
| 5,984,940 A | 11/1999 | Davis et al. |
| 5,997,561 A | 12/1999 | Bocker et al. |
| 6,015,392 A | 1/2000 | Douglas et al. |
| 6,022,366 A | 2/2000 | Schraga |
| 6,027,459 A * | 2/2000 | Shain et al. ................ 600/573 |
| 6,036,924 A | 3/2000 | Simons et al. |
| 6,045,567 A | 4/2000 | Taylor et al. |
| 6,048,352 A | 4/2000 | Douglas et al. |
| 6,056,701 A | 5/2000 | Duchon et al. |
| 6,056,765 A * | 5/2000 | Bajaj et al. ................. 606/181 |
| 6,063,039 A * | 5/2000 | Cunningham et al. ...... 600/573 |
| 6,066,103 A * | 5/2000 | Duchon et al. ............. 600/583 |
| 6,071,249 A | 6/2000 | Cunningham et al. |
| 6,071,250 A * | 6/2000 | Douglas et al. ............. 600/583 |
| 6,071,294 A | 6/2000 | Simons et al. |
| 6,080,116 A | 6/2000 | Erickson et al. |
| 6,086,545 A | 7/2000 | Roe et al. |
| 6,093,156 A | 7/2000 | Cunningham et al. |
| 6,099,484 A | 8/2000 | Douglas et al. |
| 6,143,164 A | 11/2000 | Heller et al. |
| 6,152,889 A | 11/2000 | Sopp et al. |
| 6,152,942 A | 11/2000 | Brenneman et al. |
| 6,156,050 A | 12/2000 | Davis et al. |
| 6,156,051 A | 12/2000 | Schraga |
| 6,183,489 B1 * | 2/2001 | Douglas et al. ............. 600/583 |
| 6,210,421 B1 | 4/2001 | Bocker et al. |
| 6,261,244 B1 | 7/2001 | Kensey et al. |
| 6,283,982 B1 | 9/2001 | Levaughn et al. |
| 6,306,104 B1 | 10/2001 | Cunningham et al. |
| 6,306,152 B1 | 10/2001 | Verdonk et al. |
| 6,315,738 B1 | 11/2001 | Nishikawa et al. |
| 6,319,210 B1 * | 11/2001 | Douglas et al. ............. 600/583 |
| 6,332,871 B1 | 12/2001 | Douglas et al. |
| 6,346,114 B1 | 2/2002 | Schraga |
| 6,352,514 B1 | 3/2002 | Douglas et al. |
| 6,419,661 B1 | 7/2002 | Kuhr et al. |
| 6,423,011 B1 | 7/2002 | Arulkumaran et al. |
| 6,464,649 B1 | 10/2002 | Duchon et al. |
| 2001/0011157 A1 | 8/2001 | Latterell et al. |
| 2001/0027327 A1 | 10/2001 | Schraga |
| 2001/0039387 A1 | 11/2001 | Rutynowski et al. |
| 2001/0044615 A1 | 11/2001 | Amano et al. |
| 2002/0002344 A1 | 1/2002 | Douglas et al. |
| 2002/0004196 A1 | 1/2002 | Whitson |
| 2002/0022789 A1 | 2/2002 | Perez et al. |
| 2002/0029059 A1 | 3/2002 | Purcell |
| 2002/0040230 A1 | 4/2002 | Kuhr et al. |
| 2002/0077584 A1 | 6/2002 | Lin et al. |
| 2002/0082522 A1 | 6/2002 | Douglas et al. |
| 2002/0103499 A1 | 8/2002 | Perez et al. |
| 2002/0115967 A1 | 8/2002 | Svedman |
| 2002/0169470 A1 | 11/2002 | Kuhr et al. |

FOREIGN PATENT DOCUMENTS

| | | |
|---|---|---|
| EP | 0 453283 A1 | 10/1991 |
| EP | 0 622 046 B1 | 2/1994 |
| EP | 0 671 146 A1 | 9/1995 |
| EP | 0 688 532 A2 | 12/1995 |
| JP | 08000598 | 1/1996 |
| JP | 0200116768 A1 | 4/2000 |
| WO | WO 8504089 | 9/1985 |
| WO | WO 93/09723 | 5/1993 |
| WO | WO 95/10223 | 4/1995 |
| WO | WO 96/37256 A1 | 11/1996 |
| WO | WO 97/08986 A1 | 3/1997 |
| WO | WO 97/42882 | 11/1997 |
| WO | WO 97/42885 A1 | 11/1997 |
| WO | WO 97/43962 | 11/1997 |
| WO | WO01/64105 A1 | 9/2001 |

OTHER PUBLICATIONS

Korthuis, et al., "Interstitium & Lymphatic Techniques", pp. 326–327.

Turner, et al., "Diabete Mellitus: Biosensors for", Biosensors, pp. 85–115 (1985).

"Microlet Choice" Low Pressure Blood Sampling Instrument Ad with Translation, Jun. 1997.

* cited by examiner

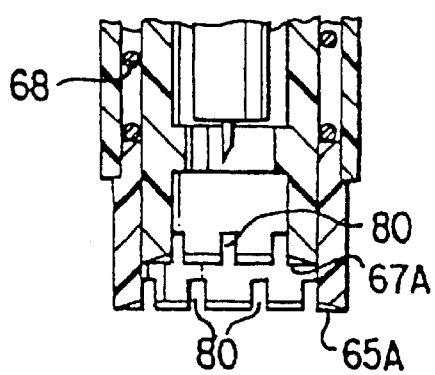 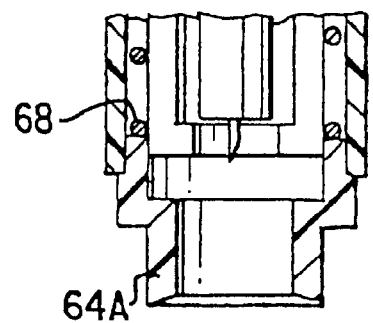
FIG. 7  FIG. 8
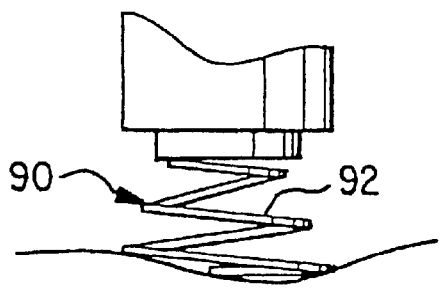 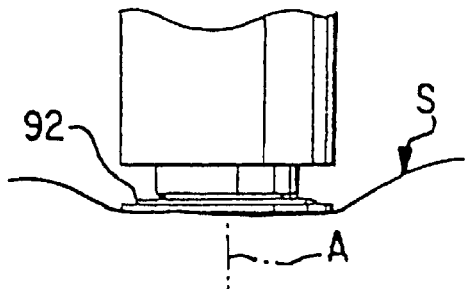
FIG. 9  FIG. 11
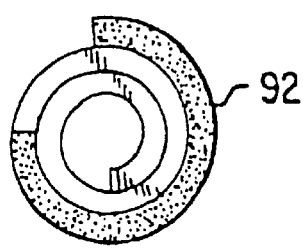 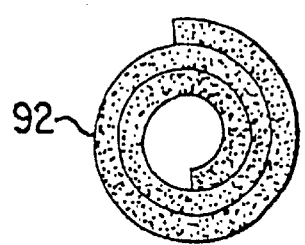
FIG. 10  FIG. 12

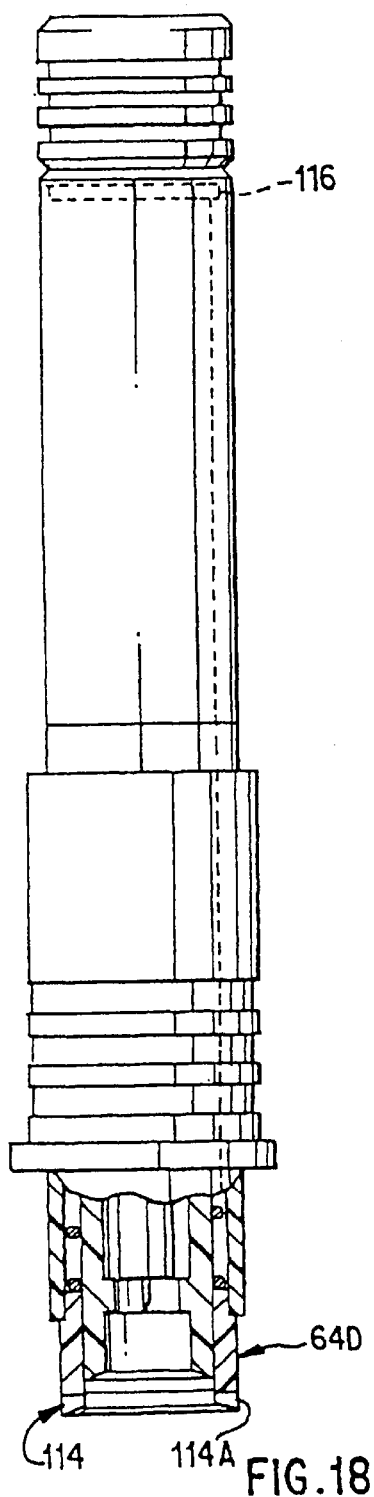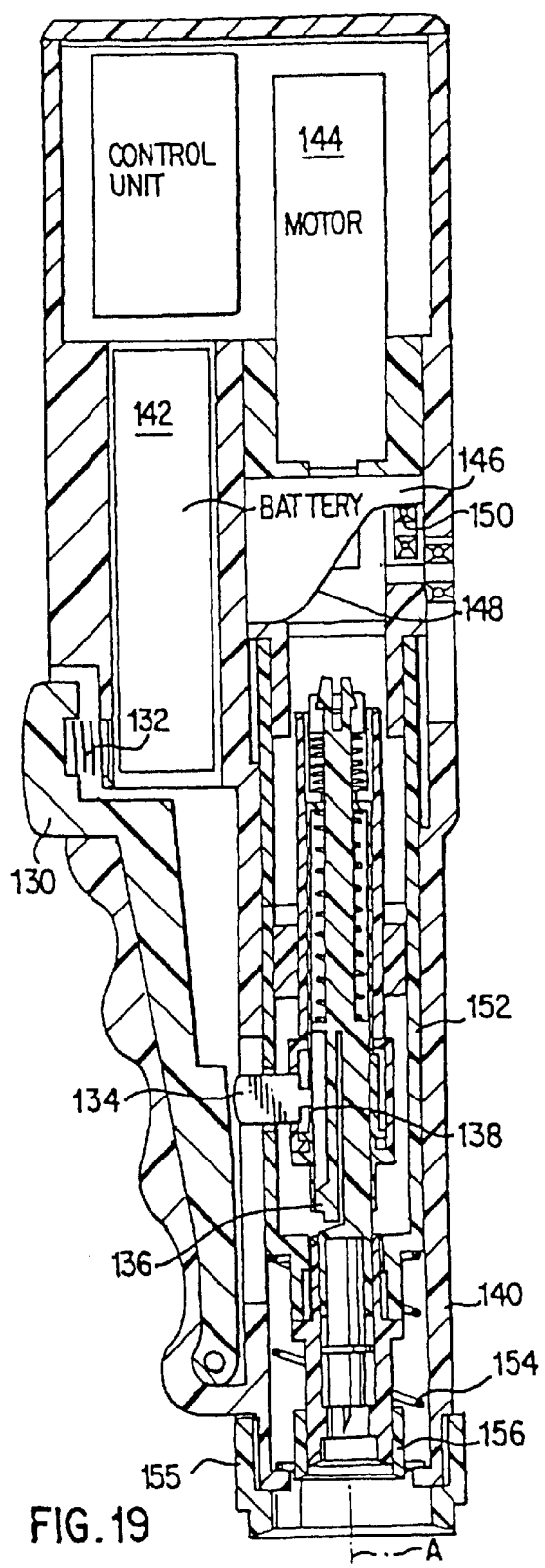
FIG. 18
FIG. 19

METHODS AND APPARATUS FOR EXPRESSING BODY FLUID FROM AN INCISION

PRIOR APPLICATIONS

The present application is a continuation-in-part of co-pending U.S. patent application Ser. No. 09/542,040 filed Mar. 31, 2000, now U.S. Pat. No. 6,464,649, the entirety of which is hereby incorporated by reference, which is a continuation of U.S. patent application Ser. No. 09/285,021, filed Apr. 1, 1999, now U.S. Pat. No. 6,066,103, which is a continuation of U.S. patent application Ser. No. 08/975,978, filed Nov. 21, 1997, now U.S. Pat. No. 5,964,718.

FIELD OF THE INVENTION

This invention relates to a body fluid testing device and methods for obtaining samples of blood fluid for analysis.

BACKGROUND OF THE INVENTION

Many medical procedures in use today require a relatively small sample of body fluid, for example in the range of 0.1–50 micro liters. It is more cost effective and less traumatic to the patient to obtain such a sample by lancing or piercing the skin at a selected location, such as the finger or forearm, to enable the collection body fluid. With the advent of home use tests for the self monitoring of blood glucose, there is a requirement for a simple procedure which can be performed in any setting without a person needing the assistance of a professional.

One device which is commonly utilized to form an opening in the patient's skin is a lancets. Lancets generally have a rigid body and a sterile lance which protrudes from one end. The lancet may be used to pierce the skin, thereby enabling the collection of a body fluid sample from the opening created. The body fluid sample is transferred to a test device or collection device. Body fluid is most commonly taken from the fingertips, where the supply is generally excellent. However, the nerve density in this region causes significant pain in many patient's. Sampling of alternative sites, such as earlobes and limbs is sometimes practiced to lessen the pain. These sites are also less likely to provide excellent body fluid samples and make body fluid transfer directly to test devices difficult. Examples of body fluids which may be utilized to test for glucose are blood and interstitial fluid.

Repeated lancing in limited surface areas, such as fingertips, results in callous formation. This leads to increased difficulty in drawing body fluid and increased pain.

To reduce the anxiety of piercing the skin and the associated pain, many spring loaded devices have been developed wherein the device automatically triggers in response to an applied force. Thus the user cannot anticipate the exact timing of the piercing, thus they are less likely to pull the device away during use. The following two patents are representative of the devices which were developed in the 1980's for use with home diagnostic test products.

U.S. Pat. No. 4,503,856, Cornell et al., describes a spring loaded lancet injector. The reusable device interfaces with a disposable lancet. The lancet holder may be latched in a retracted position. When the user contacts a release, a spring causes the lancet to pierce the skin at high speed and the retract. The speed is important to reduce the pain associated with the puncture.

Levin et al., U.S. Pat. No. 4,517,978 describes a blood sampling instrument. This device, which is also spring loaded, uses a standard disposable lancet. The design enables easy and accurate positioning against a fingertip so the impact site can be readily determined. After the lancet pierces the skin, a bounce back spring retracts the lancet to a safe position within the device.

In home settings it is often desirable to collect a body fluid sample in order to enable a user to perform a test at home, such as glucose monitoring. Some blood glucose monitoring systems, require that the blood sample be applied to a test device wich is in contact with the test instrument. In such situations, bringing the finger to the test device poses some risk of contamination of the sample with a previous sample that may not have been properly cleaned from the device. Glucose monitoring devices may utilize a blood sample in many ways, though the two most common methods for collection are a paper strip and a capillary tube. Monitors that utilize a paper strip, require the patient to pierce a finger or appropriate location, withdraw a small sample of blood from the pierced area, such as by squeezing, and then placing the paper strip in physical contact with the blood sample and waiting until the paper strip absorbs the blood. Monitors that utilize a capillary tube for fluid collection, require the patient to follow the process described above, except that a paper strip is not utilized, instead a small capillary tube is placed over the sample until a sufficient amount of blood is withdrawn into the capillary tube and to the glucose testing area of the testing device.

Many times due to dexterity problems or poor eye site it can be difficult for the patient to either bring the body fluid sample to the testing area or to bring a capillary tube to the fluid sample. Additionally, some patient's have a fear of bodily fluids, such as blood, and would prefer not to see this type of body fluid.

Amira Medical Inc. introduced a new method for home glucose testing. Amira's device AtLast 7, tests blood glucose levels by taking blood from the skin of the forearm, which is a much less sensitive than the fingertips. This device has been very well received by both the diabetic community as well as the blood glucose measurement industry.

Haynes, U.S. Pat. No. 4,920,977 describes a blood collection assembly with a lancet and micro-collection tube. This device incorporates a lancet and collection container in a single device. The lancing and collection are two separate activities, but the device is a convenient single disposable unit for situations when sample collection prior to use is desirable. Similar devices are disclosed in Sarrine. U.S. Pat. No. 4,360,016 and O'Brian, U.S. Pat. No. 4,924,879.

Jordan et al., U.S. Pat. No. 4,850,973 and U.S. Pat. No. 4,858,607 disclose a combination device which may be alternatively used as a syringe-type injection device and a lancing device with disposable solid needle lancet, depending on configuration.

Lange et al., U.S. Pat. No. 5,318,584 describes a blood lancet device for withdrawing blood for diagnostic purposes. This invention uses a rotary/sliding transmission system to reduce the pain of lancing. The puncture depth is easily and precisely adjustable by the user.

Suzuki et al., U.S. Pat. No. 5,368,047, Dombrowski, U.S. Pat. No. 4,654,513 and Ishibashi, et al., U.S. Pat. No. 5,320,607 each describe suction-type blood samplers. These devices develop suction between the lancing site and the end of the device with the lancet holding mechanism withdraws after piercing the skin. A flexible gasket around the end of the device helps seal the end around the puncture site until adequate sample is withdrawn from the puncture sire or the user pulls the device back.

Garcia et al., U.S. Pat. No. 4,637,403 discloses a combination lancing and blood collection device which uses a capillary action passage to conduct body fluid to a separate test strip in the form of a micro porous membrane. It is necessary to achieve a precise positioning of the upper end of the capillary passage with respect o the membrane in order to ensure that the body fluid from the passage is transferred to the membrane. If an appreciable gap exits therebetween, no transfer may occur.

It is difficult for a user to determine whether a sufficiently large drop of body fluid has been developed at the incision for providing a large enough sample.

Single use devices have also been developed for single use tests, i.e. home cholesterol testing, and for institutional use to eliminate the cross-patient contamination multi-patient use. Crosman et al., U.S. Pat. No. 4,869,249, and Swierczek, U.S. Pat. No. 5,402,798, also describe disposable, single use lancing devices.

The disclosures of the above patents are incorporated herein by reference.

An object of the present invention is to provide a one-step procedure and device for testing glucose levels in body fluids.

Another object of the present invention is to provide an apparatus that withdraws a body fluid sample and provides an individual with a body fluid glucose level reading.

Even with the many improvements which have been made, the pain associated with lancing remains a significant issue for many patients. The need for blood sampling and the fear of the associated pain is also a major obstacle for the millions of diagnosed diabetics, who do not adequately monitor their blood glucose due to the pain involved. Moreover, lancing to obtain a blood sample for other diagnostic applications is becoming more commonplace, and a less painful, minimally invasive device is needed to enhance those applications and make those technologies more acceptable.

An object of the present invention therefore, is to provide a device and a method for obtaining a sample of bodily fluid through the skin which is virtually pain free and minimally invasive, particularly by penetrating less sensitive areas of the skin.

Furthermore, known lancing devices include manually actuable buttons for triggering the lance-driving mechanism once the user has placed the device against his/her skin. Because the user knows the precise instant when the lancet will be triggered and pain will be felt, there is a tendency for the user to jerk or raise the device at the instant of triggering, which can lead to inconsistent skin penetration, or possibly no penetration. Therefore, a further object of the invention is to provide a lancing device which eliminates such a tendency on the part of the user.

Therefore, it is another object of the invention to provide a lancet carrier which eliminates the above-mentioned shortcomings.

Another object of this invention is to provide a method which can result in a sample of either blood or interstitial fluid, depending on the sample site and the penetration depth utilized. While there are no commercially available devices utilizing interstitial fluid (ISF) at this time, there are active efforts to establish the correlation of analytes, such as glucose, in ISF compared to whole blood. If ISF could be readily obtained and correlation is established, ISF may be preferable as a sample since there is no interference of red blood cells or hematocrit adjustment required.

Another object of this invention is to provide a method by which the drawn sample is collected and may be easily presented to a testing device, regardless of the location of the sample site on the body. This approach helps with infection control in that multiple patients are not brought in contact with a single test instrument; only the sampling device with a disposable patient-contact portion is brought to the test instrument. Alternatively, the disposable portion of a test device may be physically coupled with the sampler so the sample can be brought directly into the test device during sampling. The test device may then be read in a test instrument if appropriate or the testing system can be integrated into the sampler and the test device can provide direct results displayed for the patient.

It is a further object of the invention is to provide a device for minimally invasive sampling comprising a reusable sampler and disposable sample lancet and collection device.

SUMMARY OF THE INVENTION

The present invention involves a method of obtaining a sample of fluid from a body. The method comprises applying a skin-lancing medium against a skin surface to form an incision therein, removing the skin-lancing medium from the incision; and thereafter applying a force to depress the skin in a manner forming a ring of depressed body tissue in surrounding relationship to the incision, causing the incision to bulge and the sides of the incision to open, whereby body fluid is forced out through the opening of the incision.

The invention also relates to a device for sampling body fluid which comprises a housing having an open end, and a skin lancing mechanism for applying a skin-lancing medium against a skin surface to form an incision therein and then remove the skin-lancing medium from the incision. A stimulator member is mounted to the housing at the open end thereof for movement relative to the housing. The stimulator member extends about a longitudinal axis of the housing and is adapted to engage the skin surface to bulge and open the incision in response to a pressing of the end face against the skin surface.

The invention also relates to a device for expressing body fluid from a lanced skin surface, which comprises a housing, and a stimulator mechanism mounted to the housing at an end thereof. The stimulator mechanism includes a generally circular array of stimulator elements each mounted to the housing for movement toward and away from a longitudinal axis of the housing. An actuator is mounted to the housing for displacing the stimulator elements toward the axis.

The invention also relates to a device for expressing body fluid from a lanced skin surface, which comprises a housing and a stimulator member mounted on the housing at an end thereof. The stimulator member comprises a coil spring which is compressible toward the housing in response to being pushed against a user's skin in surrounding relationship to a lanced portion thereof.

Another aspect of the invention relates to a device for expressing body fluid from a lanced skin surface which comprises a housing and a hollow stimulator member mounted at an end of the housing and adapted to engage a user's skin surface in surrounding relationship to a lanced portion thereof. In order to promote the flow of body fluid, the stimulator member can be heated, or vibrated. If vibrated, the stimulator member applies an ultrasonic frequency to the skin surface.

The invention also relates to a device for expressing body fluid from a lanced skin surface which comprises a housing and a hollow stimulator member mounted at an end of the housing for longitudinal movement relative to the housing and adapted to contact a user's skin surface in surrounding relationship to a lanced portion thereof. A motor is mounted in the housing and a reciprocatory mechanism is connected to the motor to be driven thereby, and is operably connected to the stimulator member for reciprocating the stimulator member along a longitudinal axis of the stimulator member.

BRIEF DESCRIPTION OF THE DRAWING

The objects and advantages of the invention will become apparent from the following detailed description of preferred embodiments thereof in connection with the accompanying drawing in which like numerals designate like elements and in which:

FIG. 7 is a fragmentary longitudinal sectional view through a second embodiment of the invention;

FIG. 8 is a fragmentary longitudinal sectional view taken through a third embodiment of the invention;

FIG. 9 is a side elevational view of a fourth embodiment of the invention pressed against a skin surface;

FIG. 10 is an end view of the device depicted in FIG. 9;

FIG. 11 is a view similar to FIG. 9 after the device has been compressed against the skin surface to bulge and open an incision;

FIG. 12 is an end view of the device in the condition depicted in FIG. 11;

FIG. 18 is a side elevational view, partly in longitudinal section of yet another embodiment of the invention;

FIG. 19 is a longitudinal sectional view taken through still a further embodiment of the invention;

DETAILED DESCRIPTION OF A PREFERRED EMBODIMENT

Figures 1, 2:
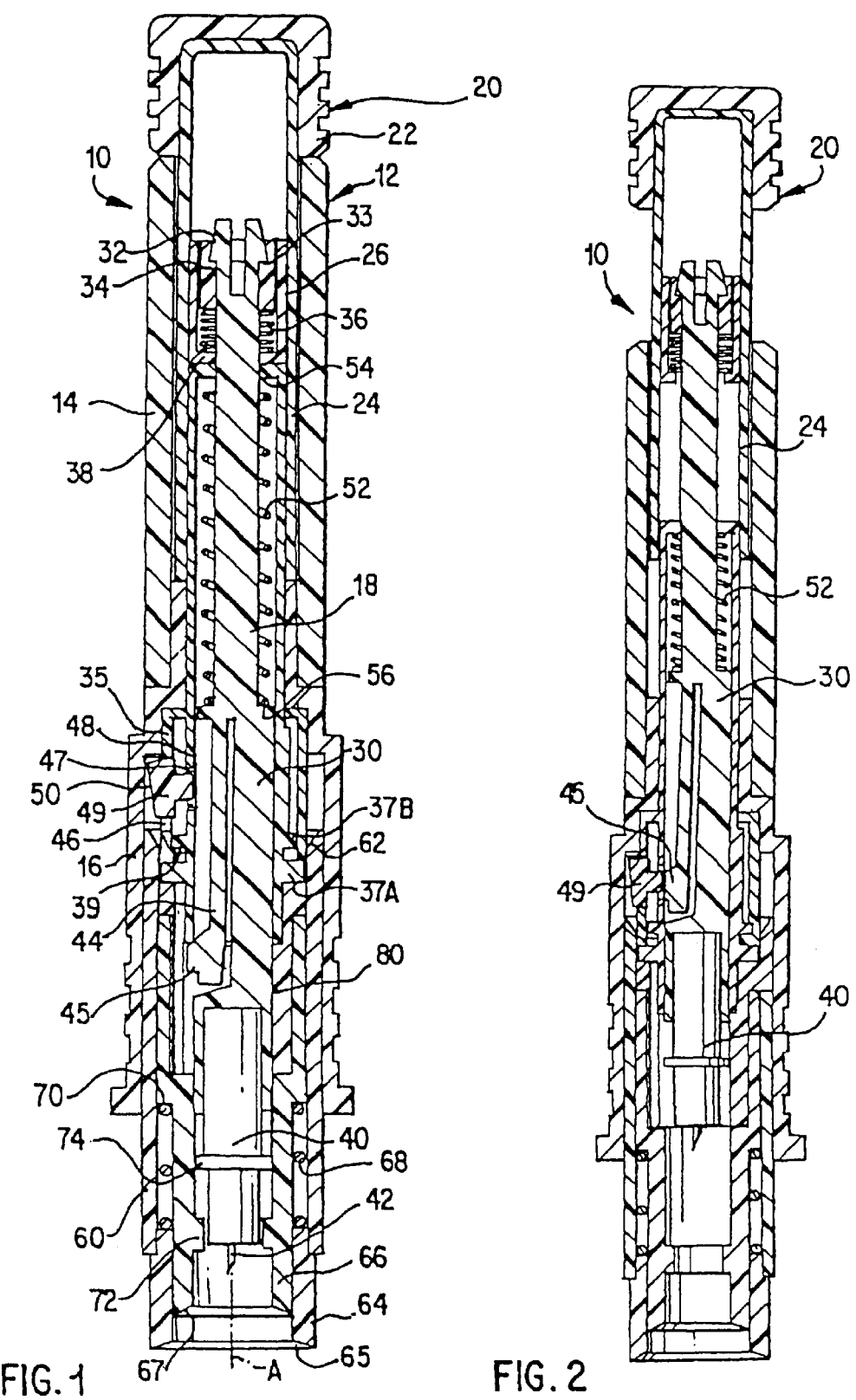
FIG. 1 is a longitudinal sectional view through a blood sampling device according to a first embodiment of the invention, with the lancet carrier in an unarmed condition.
FIG. 2 is a view similar to FIG. 1, with the lancet carrier in an armed condition.

A lancing device 10 (see FIG. 1) according to one preferred embodiment of the invention comprises an outer housing 12 having upper and lower portions 14, 16 connected together, and an inner housing 18 fixed to the outer housing.

Mounted for vertical reciprocation in the upper portion 14 of the outer housing 12 is a cocking mechanism 20 comprising a pull handle 22 to which is fixedly secured a hollow draw tube 24. Fixed to an inner wall of the draw tube 24 is a draw ring 26.

Situated within the draw tube 24 is a draw bar 30 having a pair of flexible hooks 32 at its upper end. The hooks are releasably latched to a sleeve 34 which is movably disposed within the draw ring 26. A coil compression spring 36 acts between a flange 33 of the sleeve 34 and an inner flange 38 of the draw ring 26.

A trigger sleeve 35 is mounted within the lower portion 16 of the outer housing 12. A lower end of the trigger sleeve rests upon a first outer flange 37A of the inner housing, and a second outer flange 37B of the inner housing rests upon an inner projection 39 of the trigger sleeve.

At its lower end the draw bar 30 frictionally holds a skin-lancing medium in the form of a disposable lancet 40 in which a needle 42 is disposed. The draw bar 30 includes a flexible latch finger 44 that has a projection 45 adapted to be received in a hole 46 of the inner housing 18 (see FIG. 2) when the device is armed. A trigger member 49 is mounted in a hole 47 of the trigger sleeve 35 and includes an arm 48 extending partially into the hole 46. The trigger member 49 includes an inclined cam follower surface 50.

A coil compression spring 52 acts between a top wall 54 of the inner housing 18 and a shoulder 56 of the draw bar.

Slidably disposed within a lower end of the lower portion of the outer housing is a firing tube 60 which includes an upper cam surface 62. Fixed to a lower end of the firing tube 60 is an outer hollow stimulator member in the form of a cylindrical ring 64, having an end surface 65 of generally frusto-conical shape so as to be oriented at a downward and inward inclination to generally face a longitudinal axis A of the device.

Disposed coaxially within the firing tube 60 and outer stimulator ring 64 is an inner hollow stimulator member also in the form of a cylindrical ring 66 having a frusto-conical end surface 67 also oriented at a downward and inward inclination.

The end surfaces 65 and 67 are of circular configuration when viewed along the axis A, other configurations, such as polygonal, oval, etc., are possible.

A coil compression spring 68 acts between an upper end of the outer stimulator ring 64 and a downwardly facing shoulder 70 of the inner stimulator ring 66.

The inner stimulator ring 66 includes a lance stop flange 72 adapted to be engaged by a lance ring 74 of the lancet 40 as will be explained.

The first flange 37A of the inner housing rests upon a support sleeve 80 which, in turn, rests upon an upper end of the inner stimulator ring 66.

In practice, when a fluid sample, such as blood or interstitial fluid, is to be taken from a user's body, a lancing device according to the present invention can be used to minimize pain. To do so, a region of the user's body having less sensitivity than, for example, a fingertip, is selected. Such a low-sensitivity region could be the user's forearm for example. Initially, the handle 22 is pulled up to raise the drawbar 30 until the projection 45 of the latch finger 44 snaps into the hole 44 of the inner housing 18, as shown in FIG. 2. Simultaneously, the spring 52 is compressed.

Figure 3:
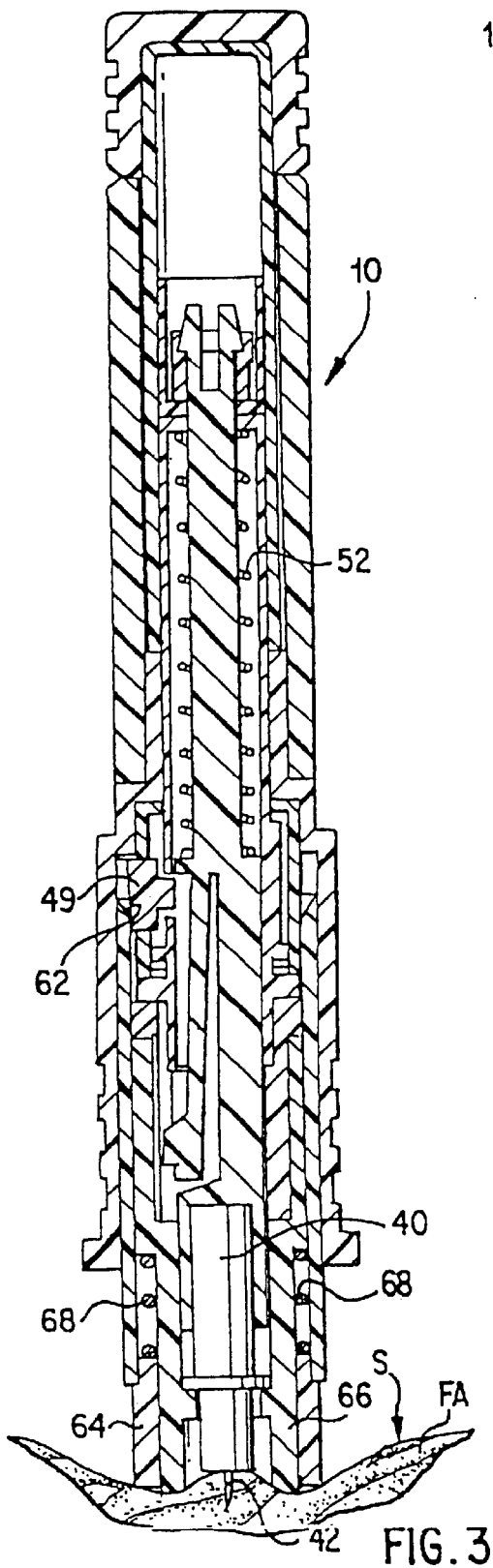
FIG. 3 is a view similar to FIG. 2 after the lancet carrier has been triggered and a lancet is penetrating the skin.

If the outer stimulator ring 64 is pressed against the user's skin S, e.g., on the selected forearm region FA, the ring 64 and its cam surface 62 are moved upwardly to displace the trigger radially inwardly, whereupon the projection 45 of the latch finger 44 is disengaged from the hole 46. Accordingly, the spring 52 expands to displace the drawbar 30 downwardly so that the needle 42 punctures the skin sufficiently deep to cut capillaries in the superficial vascular plexus, as shown in FIG. 3. Simultaneously, the spring 68 is compressed. The extent of displacement of the drawbar 30 is limited by engagement between the lance ring 74 with the lance stop 72.

Figure 4:
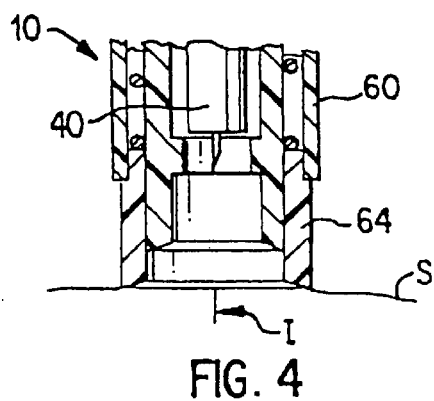
FIG. 4 is a fragmentary view similar to FIG. 1 after an incision has been formed.

Once lancing has occurred, the compressed spring 68 expands to raise the drawbar, as well as the needle 42 and inner stimulator ring 66 from the skin (see FIG. 4).

Figure 5:
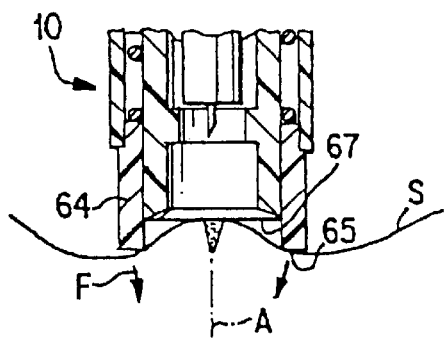
FIG. 5 is a view similar to FIG. 4 showing a stimulator member of the device being depressed to cause the incision to bulge and open.

The user then alternately applies and releases a downward force on the outer housing 12. Each time that a downward force is applied, the end face 65 of the outer stimulator ring 64 exerts a downward force F which depresses a ring-shaped portion of the skin and body tissue which is disposed in surrounding relationship to the wound or incision I, causing the wounded area to bulge while pulling apart the sides of the wound (see FIG. 5). Hence, fluid such as blood or interstitial fluid is trapped and pressurized so that it travels upwardly through the pulled-open end of the wound since the surrounding ring of depressed skin and body tissue restricts the outward flow of fluid. That action is enhanced by the fact that the force F is inclined inwardly toward the axis A to force the fluid toward the bulged area.

Figure 6:
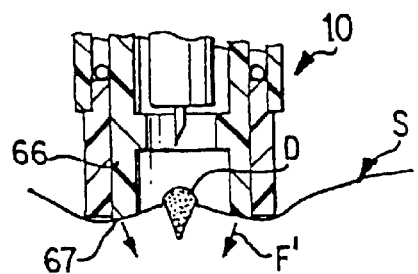
FIG. 6 is a view similar to FIG. 5 after a stimulating action has been performed to form a drop of blood at the open end of the incision.

When the downward force is released, the sides of the wound close, and fresh fluid flows toward the area of the wound to replace fluid which had been forced upwardly through the wound. As the downward force is reapplied, the above-described action is repeated and additional fluid is forced through the wound. Eventually, this "pumping" action results in the formation of a suitably large drop D of fluid (FIG. 6).

It will thus be appreciated that the present invention enables an ample supply of blood, interstitial fluid or other body fluid to be obtained relatively painlessly from areas of the body which typically possess lesser amounts of such fluid as compared with the highly sensitive fingertip region.

Note that each time that the downward force is applied to the outer housing, the outer stimulator ring 64 moves upwardly relative to the inner stimulator ring 66 so that the end surface 67 of the inner ring 66 also contacts the skin surface S at a location inwardly of the outer face 65, thereby promoting the displacement of fluid inwardly toward the wound. However, the present invention can be practiced by a single stimulator ring arrangement 64A as shown in FIG. 8.

While the surfaces 65, 67 are continuous, i.e., non-interrupted, it may be desirable to provide either or both of those surfaces with circumferentially spaced recesses 80 as shown in FIG. 7. The surface(s) 65A, 67A will still depress a ring of body tissue surrounding the wound, but the areas of the ring corresponding to the location of the recesses will be depressed to a lesser extent than the other areas. Those lesser depressed areas will provide less resistance to fluid flow and will thus enable some fluid to leak past the ring, which would be beneficial in the event that the user neglects to release the downward pressure on the device.

The stimulator member need not be in the form of a ring. As depicted in FIGS. 9–12, the stimulator member can be in the form of a helical spring 90 formed by a flat strip 92. Such a spring would function in somewhat similar fashion to the double-ring arrangement of FIGS. 1–7 in that a stimulator surface gradually comes into contact with the skin in a radially inward direction to aid in propelling blood or interstitial fluid toward the center axis. In that regard, FIGS. 9 and 10 depict a condition when the spring 90 is uncompressed. In contrast, FIGS. 11 and 12 depict a condition wherein the spring is fully compressed. Shaded regions in FIGS. 10 and 12 represent contact between the spring and the skin. It will be appreciated that during compression of the spring, the contact region of the spring progresses gradually radially inwardly, causing blood or interstitial fluid to be pushed toward the axis A and thus toward the bulged area of the skin.

Figure 13:
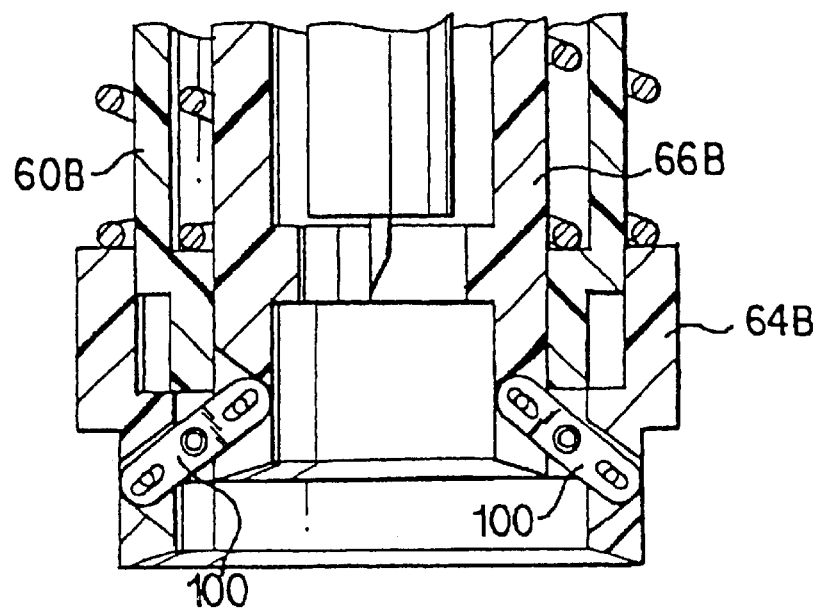
FIG. 13 is a fragmentary longitudinal sectional view taken through a fifth embodiment of the invention while in a first state of operation.
Figure 14:
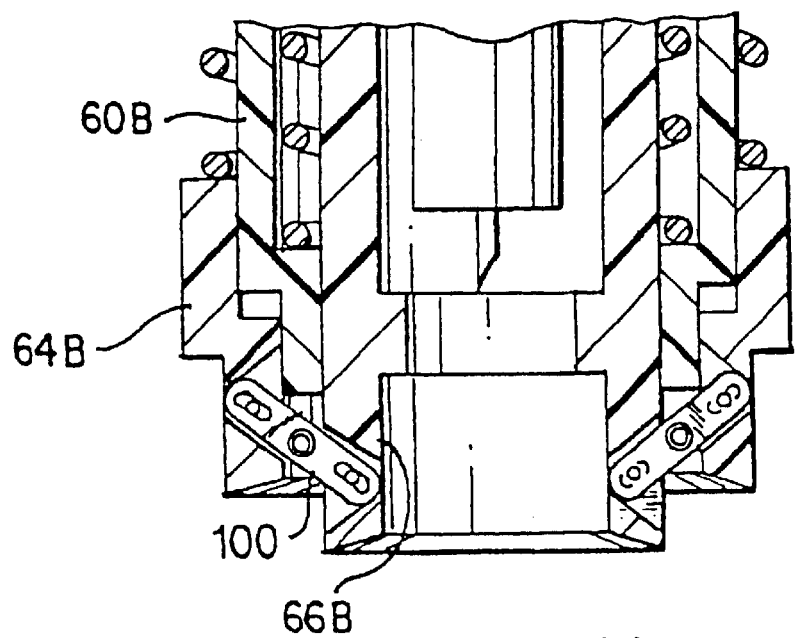
FIG. 14 is a view similar to FIG. 13 with the device in a second condition of operation.

Depicted in FIGS. 13 and 14 is yet another alternative embodiment wherein the outer stimulator ring 64B is interconnected to the inner stimulator ring 66B by levers 100 which are pivoted to the firing tube 60B. Thus, upward sliding movement of the outer ring 64B is transmitted as a downward force to the inner ring 66B to slide the latter downwardly and intensify the pumping action.

Figure 15:
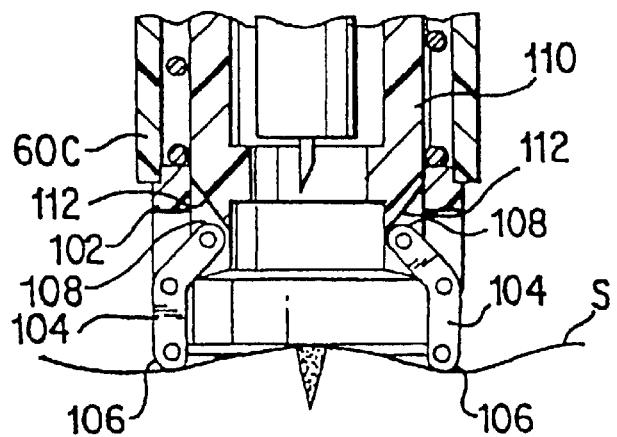
FIG. 15 is a fragmentary longitudinal sectional view taken through a sixth embodiment of the invention in a first condition of operation thereof.
Figure 16:
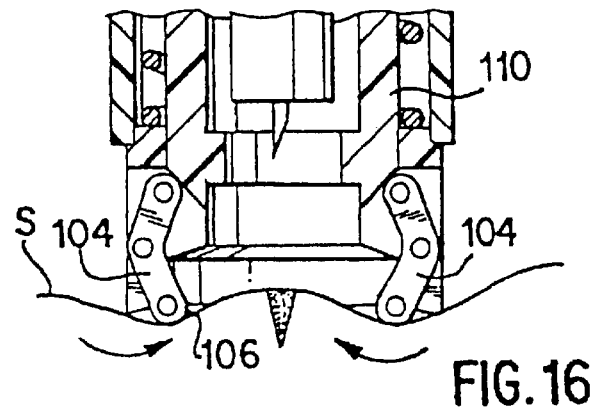
FIG. 16 is a view similar to FIG. 15 with the device in another condition of operation.
Figure 17:
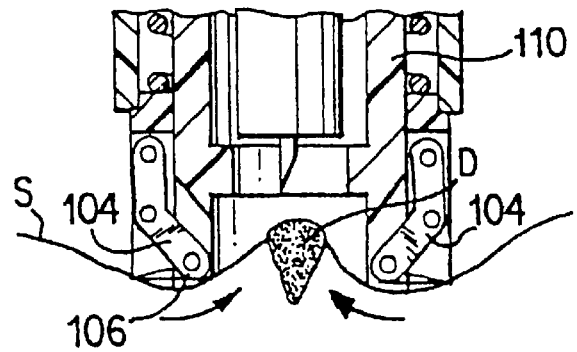
FIG. 17 is a view similar to FIG. 16 of yet a further condition of operation of the device.

A further embodiment is depicted in FIGS. 15–17 wherein the firing tube 60C has a carrier tube 102 affixed at a lower end thereof. Pivotably mounted on the carrier tube 102 is a circular array of levers 104 each having an upper and lower end, each lower end carrying a stimulator element in the form of a roller 106. Each lever 104 is rotatable about an axis extending orthogonally relative to the axis of the housing.

An inner ring 110 is slidable up and down, either by manual force, or by a motor-driven cam (e.g., of the type disclosed later in connection with FIG. 19). That ring 110 has a beveled cam face 112 formed on its lower end. When the device is pressed against the skin, following a lancing procedure, the ring 110 is moved downwardly so that the cam face 112 engages rollers 108 mounted on upper ends of the levers. Hence, the levers 104 are rotated such that the lower rollers 106 are displaced inwardly and upwardly at a location disposed below the open end of the bulged wound to open the wound and force blood or interstitial fluid toward the wound to form a drop D. When the levers are not contacted by the cam face 112, the rollers 106 gravitate to a rest position shown in FIG. 15. Repeated applications of the downward force cause the drop to become gradually enlarged as explained earlier.

Depicted in FIG. 18 is an alternative embodiment similar to that depicted in FIGS. 1–6, except that the lower end surface of the outer stimulator ring 64D is provided with a hollow stimulator element 114 which is electrically connected to a battery 116 mounted in an upper end of the device. The element can be either an electrical resistance element (i.e., a heater) or a vibrator such as a piezoelectric transducer, intended to stimulate fluid flow. A heater will expand the capillaries and make the blood or interstitial fluid less viscous and thus more flowable, in order to increase the amount of the body fluid sample.

On the other hand, if the element 114 is a vibrator, such as a piezoelectric transducer, vibrations can be created which stimulate the flow of body fluid. This could be achieved by operating the transducer to produce frequencies below 28,000 cycles per second. Alternatively, ultrasonic frequencies, i.e., frequencies above 20,000 cycles per second, will create interferometric wave patterns inside the skin that cause contractions forcing fluid upwardly from the wound. The frusto-conical shape 114A of the end face of the element will optimize the creation of such wave patterns. It may be further beneficial to employ a heater, such as an infrared emitter, mounted in the housing which vasodilates the capillaries to increase blood flow. Another advantage of the use of such frequencies is that only minimal downward force to the device may be necessary since the wave patterns may produce an ample pumping action.

FIG. 19 depicts a device which is not automatically fired, but rather requires manual actuation of lever 130 against a bias of a spring 132 to force a trigger 134 to push a projection 136 out of a hole 138 (when the projection extends into that hole).

Mounted in a housing 140 of the device are a battery 142 and electric motor 144 connected to the battery to be actuated thereby. The motor 144 rotates a sleeve 146 about the axis A. The sleeve includes a cam surface 148 which engages a follower roller 150 mounted on a tube 152.

As the sleeve 146 rotates, the cam surface pushes the tube 152 downwardly against the bias of a coil compression spring 154, to push an inner stimulator ring 156 repeatedly against a skin surface, thereby pumping blood to the top of an incision in the same manner described earlier herein. The inner stimulator ring 156 reciprocates along the axis A within an outer stimulator ring 155. This embodiment eliminates the need for the user to pulsate the device up and down; the pumping operation is achieved automatically in response to actuation of the lever 130.

The cam mechanism 146 can be used in an automatically firing device, such as that disclosed in connection with FIG. 1.

Figure 20:
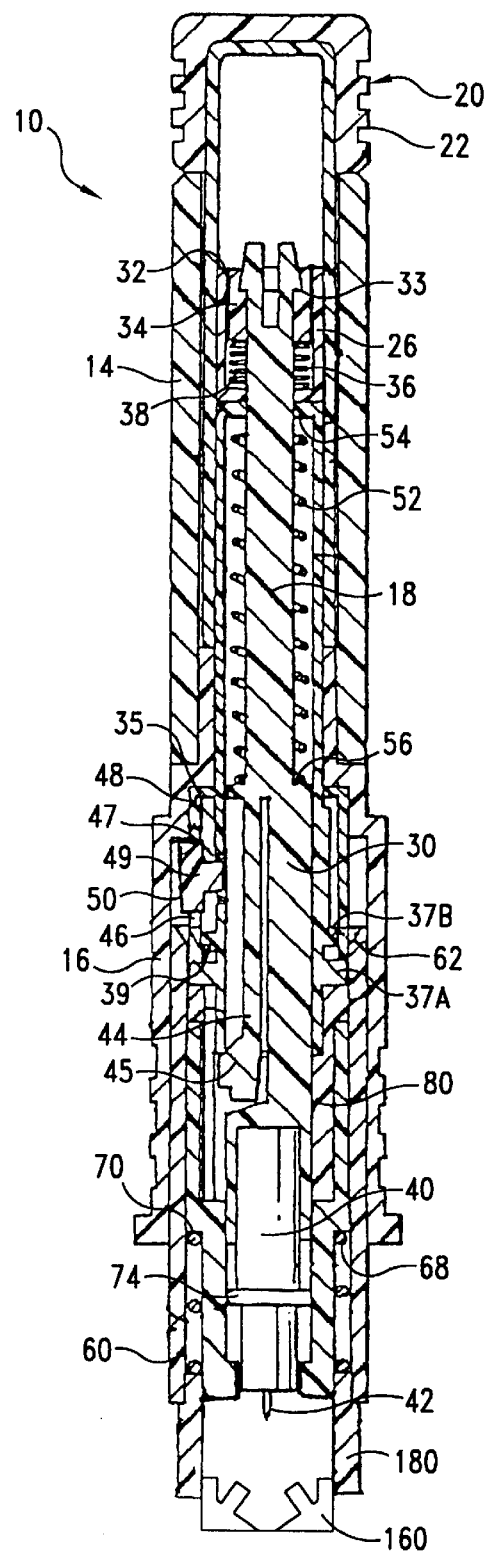
FIG. 20 is a longitudinal sectional view of a blood lancing device according to a seventh embodiment of the invention while in a first condition or operation thereof.

Referring now to FIG. 20, there is shown a seventh embodiment of the blood lancing device 10 of the present invention, wherein like reference numerals have been utilized to denote the same or similar elements of the previous embodiments described above and shown in FIGS. 1–19. The lancing device 10 according to a seventh embodiment includes an outer housing 12 having upper and lower portions 14, 16 connected together, and an inner housing 18 fixed to the outer hosing.

Mounted for vertical reciprocation in the upper portion 14 of the outer housing 12 is a cocking mechanism 20 comprising a pull handle 22 to which is fixedly secured a hollow draw tube 24. Fixed to an inner wall of the draw tube 24 is a draw ring 26.

Situated with the draw tube 24 is a draw bar 30 having a pair of flexible hooks 32 at its upper end. The hooks are releasably latched to a sleeve 34 which is movably disposed with the draw ring 26. A coil compression spring 36 act between a flange 33 of the sleeve 34 and an inner flange 38 of the draw ring 26.

A trigger sleeve 35 is mounted within the lower portion 16 of the outer housing 12. A lower end of the trigger sleeve rests upon a first outer flange 37A of the inner housing, and a second outer flange 37B of the inner housing rests upon an inner projection 39 of the trigger sleeve.

At its lower end, the draw bar 30 frictionally holds a skin-lancing medium in the form of a disposable lancet 40 in which a needle or lancet 42 is disposed. The draw bar 30 includes a flexible latch finger 44 that has a projection 45 adapted to be received in a hole 46 of the inner housing 18 when the device is armed. A trigger member 49 is mounted in a hole 47 of the trigger sleeve 35 and includes an arm 48 extending partially into the hole 46. The trigger 46 includes an inclined cam follower surface 50.

A coil compression spring 52 acts between a top wall 54 of the inner housing 18 and a shoulder 56 of the draw bar.

Figure 21:
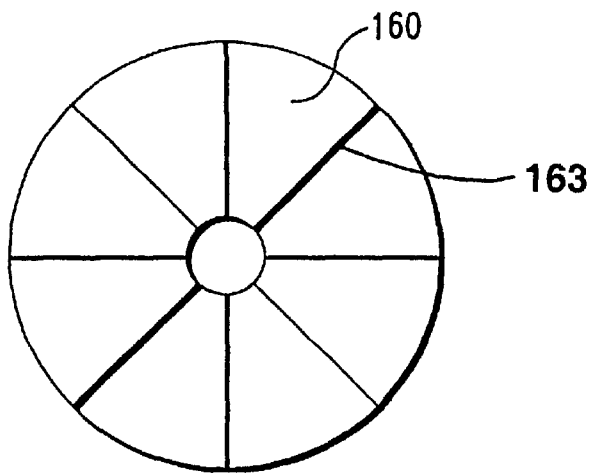
FIG. 21 is an end view of the device in the condition depicted in FIG. 20.

Slidably disposed within the lower end of the lower portion of the outer hosing is a firing tube 60 which includes an upper cam surface 62. Fixed to a lower end of the firing tube 60 is a stimulator member 160 in the form of a flexible membrane, having a tissue contacting surface 161. Referring now to FIG. 21 there is shown an end view of the lancing device 10 of the present invention illustrating the stimulator member 160. As shown, the stimulator member 160 includes circumferentially spaced interruptions 163.

Figure 22A:
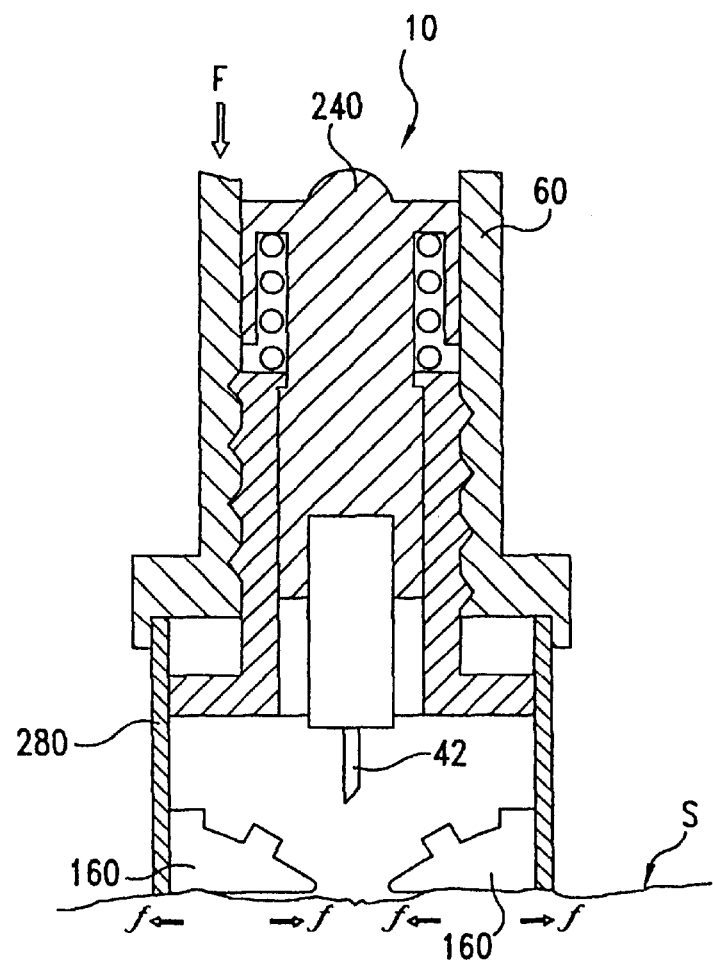
FIG. 22A is a view similar to FIG. 20, with the lancet carrier in an armed condition.
Figure 22B:
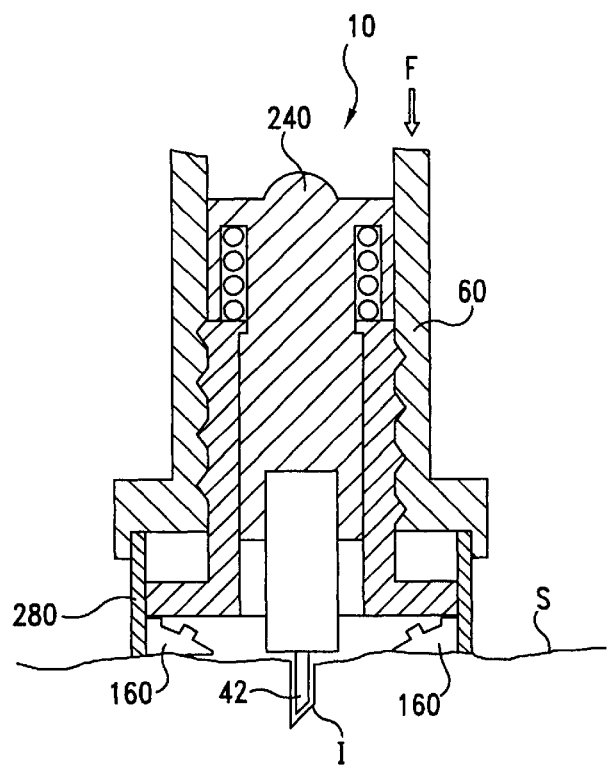
FIG. 22B is a partial cross-sectional side view of the lancing device wherein the lancet has penetrated the patient's skin.
Figure 22C:
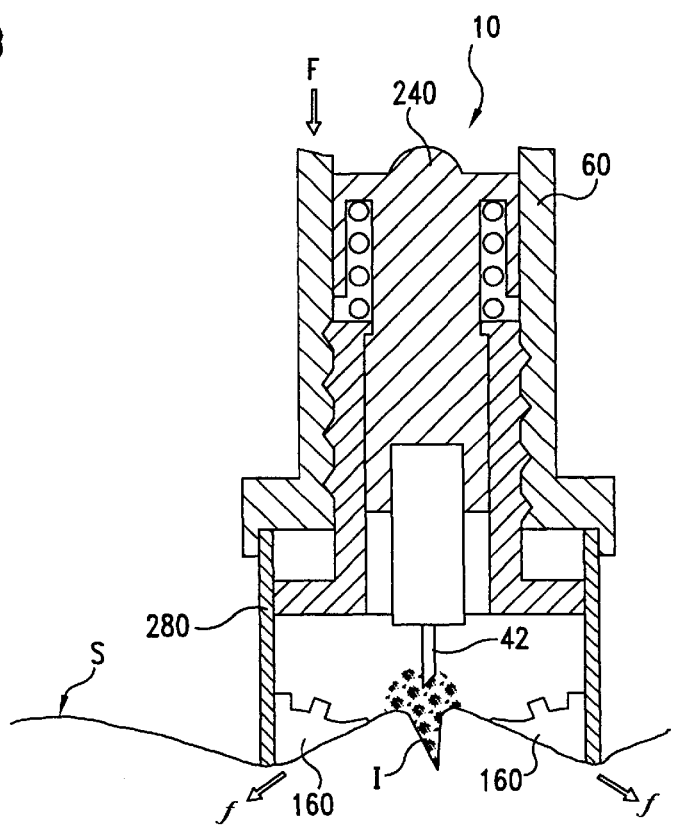
FIG. 22C is a view similar to FIG. 22A, illustrating the bulge which forms in the patient's tissue, wherein the stimulating member stretches the skin open for expressing a body fluid sample.
Figure 23:
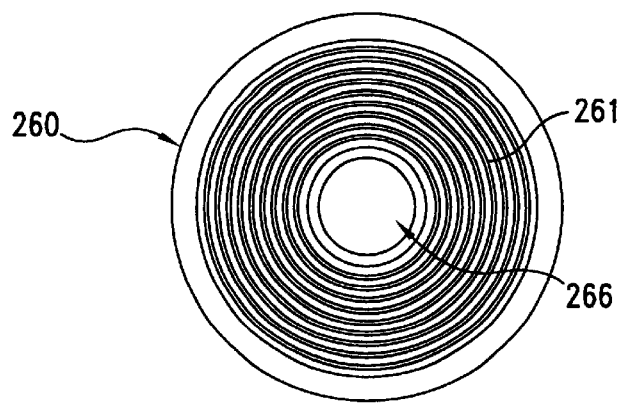
FIG. 23 is an end view of an alternative embodiment of the stimulating member of the present invention.
Figure 24:
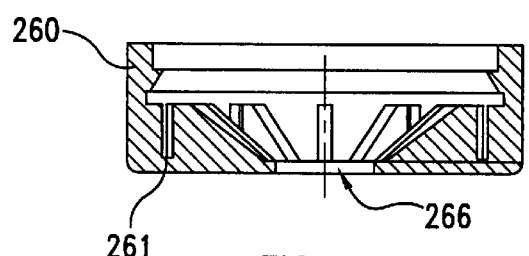
FIG. 24 is a cross-sectional side view of the alternative embodiment of the stimulating member illustrated in FIG. 23.
Figure 25:
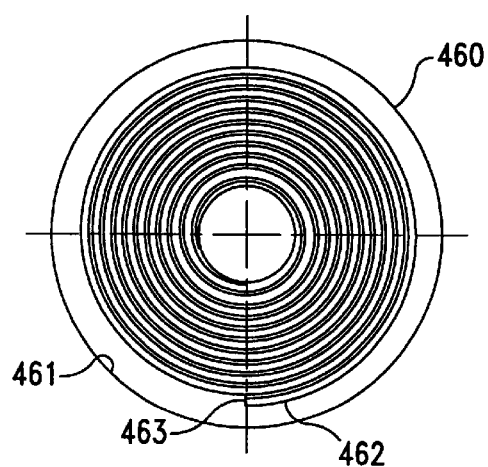
FIG. 25 is an end view of another alternative embodiment of the stimulating member of the present invention.

Referring now to FIGS. 22A through 22C, there are shown partial longitudinal cross-sectional side views of the present invention. Referring now to FIG. 22A there is shown the distal end of the lancing device 10 as disposed over a potion of skin S to be lanced in preparation for a body fluid sample to be obtained. As shown in FIG. 22A, the tissue contacting surface 161 of the stimulator member 160 contacts the patient's skin. The tissue contacting surface 161 of the stimulator member 160 may be formed having a raised area as shown in FIGS. 23–25, wherein the raised surface contact the skin S thereby providing a friction force f between the distal surface 161 and the skin S.

Referring now to FIG. 22B, wherein a force F has been applied to the proximal end of the lancing device 10, wherein the force F is translated to the lancet 42 and lancet holder 240, thereby advancing the lancet into the patient's skin.

Referring now to FIG. 22C there is shown the lancet 42 in a retracted position after the lancet 42 has penetrated the skin S to a sufficient depth to cut capillaries in the superficial vascular plexis to form an incision I as shown.

The tissue contacting surface 161 of the stimulator member 160 remains in contact with the skin as after the lancet has formed an incision within the patient's skin and is thereby withdrawn from the incision I. The force F applied to the proximal end of the lancing device 10 causes the sleeve 280 to contact the skin, wherein the skin yields to the applied force as shown in FIG. 22C. The skin S forms a bulge about the incision I formed by the lancet. The friction force f between the distal surface 161 and the skin S retains the stimulator member upon the skin S. By retaining the contacting surface 161 upon the skin S, the incision I is stretched open, thereby allowing more body fluid to be expressed from the incision. In one embodiment, the sleeve 180 causes fluid such as blood or interstitial fluid to become trapped and pressurized within the bulged area, so that the body fluid will travel upwardly through the pulled-open incision I.

After a sufficient sample size has developed, the lancing device 10 is removed from the patient's skin wherein the sample may then be utilized in any manner desirable.

It shall be understood that the stimulator member 160 and the lancing device 10 produce a sufficiently sized sample between about 0.05 micro liters and 10 micro liters without the need for repetitive motion as described above with regard to the other embodiments of the present invention. In addition, the alternative embodiment of the lancing device illustrated in FIGS. 20–22C may be utilized with other methods and devices for producing a sufficiently sized sample. For example, the lancing device 10 may include vibration means (not shown), heating means (not shown), vacuum means (not shown), each of which may be utilized to encourage blood flow within the area to be sampled. Alternatively, the area to be sampled may be stimulated using one of the methods described above prior to using the lancing device 10.

The stimulator member 160 may be constructed of biocompatible materials such as polyvinyl chloride, silicon, urethane, or similar flexible materials which are adapted to grip and translate a frictional force between the tissue contacting surface 161 and the patient's skin S thereby causing a wound to be stretched open thereby allowing a greater amount of body fluid to flow therefrom. In addition, the stimulator member 160 may be formed of materials which are flexible such that a portion of the stimulator member 160 will deform in use, though it shall be understood in a preferred embodiment, the tissue contacting surface 161 remains substantially parallel with the skin surface as shown in FIGS. 22A–22C.

Alternatively, it is contemplated that the stimulating member 160 may be formed of a rigid material wherein the skin contacting surface of the rigid stimulating member is adapted to provide a friction force between the skin and the tissue contacting surface such that the skin will be retained upon the tissue contacting surface as described above. Additionally, the stimulating member may be pivotally affixed to the sleeve 280 thereby allowing a rigid stimulator member to be utilized in the same manner as a flexible member.

Referring now to FIGS. 23 and 24 the stimulator member 260 illustrated therein may be formed in generally the same manner as that shown and described above, though the stimulator member 260 is formed having a plurality of rings 261 disposed radially about an aperture 266. In use, the plurality of rings 261 act on the skin S with a frictional force such as that described and shown above. The frictional force f retains the tissue contacting surface 261 of the stimulator member 260 upon the skin surface S, whereby causing the incision I to stretch open as described above.

Referring now to FIG. 25 there is shown yet another alternative embodiment of the stimulator member 460 of the present invention. The stimulator member 460 further includes a raised member 462 extending from the tissue contacting surface 461. The raised member 462 is disposed upon the tissue contacting surface 461 in a spiraling manner, such as that shown in FIGS. 9–11, and 25. In practice, the leading edge 463 of the spiraling raised member 462 will contact the patient's skin first, thereafter as a greater downward force is applied the remaining portion of the spiraling raised member 462 will contact the patient's tissue. The forced imparted by the spiraling raised member 462 will cause the skin to bulge, in addition the constant spiraling motion will cause the fluid under the skin to become concentrated within the center of the bulge.

Figure 26:
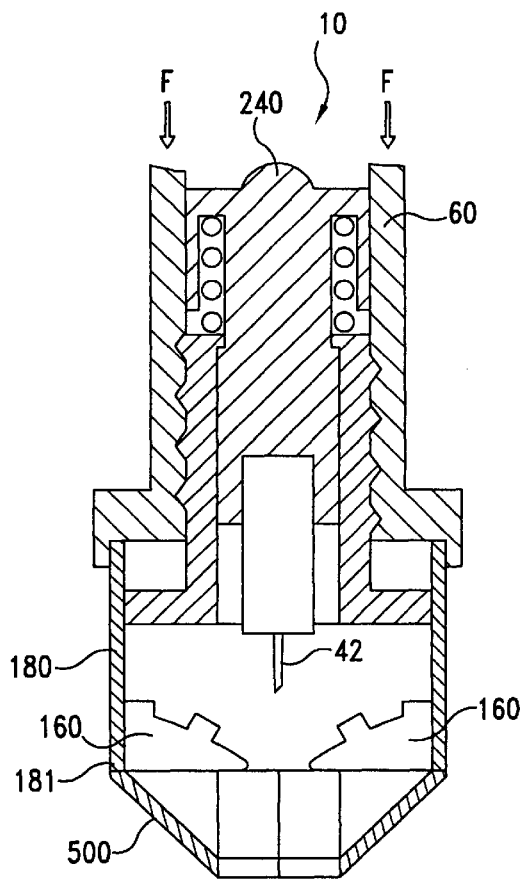
FIG. 26 is a partial cross-sectional side view of a lancing device including a stimulating member and a constricting member.
Figure 28:
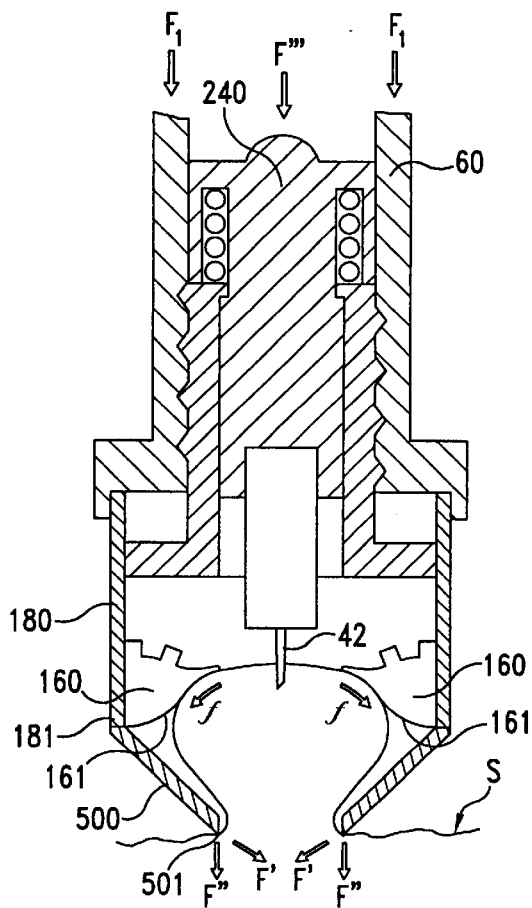
FIG. 28 is a partial cross-sectional side view of the lancing device of FIG. 26 in use illustrating a bulge of tissue formed by the constricting member.

Referring now to FIG. 26 there is shown yet another alternative embodiment in accordance with the present invention. The lancing device 10 may further include a stimulating member 160 as described in detail above with regard to FIGS. 1 through 25. In addition to the stimulating member 160, a constricting member 500 may be fixedly attached to the distal end 181 of the sleeve 180. The constricting member 500 may be constructed of a pliable material, wherein the constricting member 500 will flex as shown in FIG. 28. Examples of materials which the constricting member 500 may be constructed of plastics such as polyethylene, polysilicone, polyvinyl chloride, or alternatively of materials such as titanium, aluminum, steel, stainless steel.

The constricting member 500 may be constructed as a separate body which is then fixedly attached to the distal end 181 of the sleeve 180 with an adhesive or mechanical fastener or other process such as melting or fusion welding. Alternatively, the constricting member 500 may be pivotally attached to the distal end 181 of the sleeve 180 (not shown).

Figure 27:
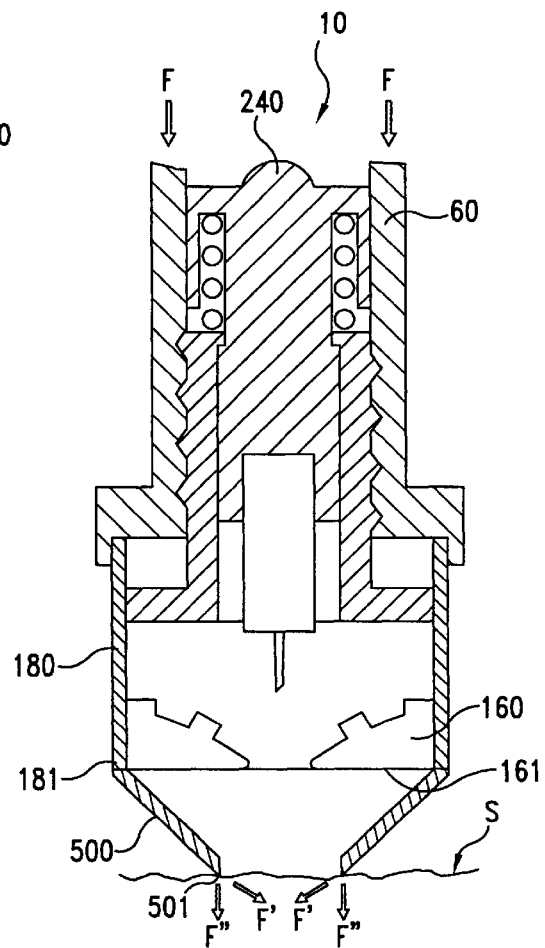
FIG. 27 is a partial cross-sectional side view of the lancing device of FIG. 26 in use.

Method of use relating to the lancing device 10 will be described in relation to FIGS. 27–29. Referring now to FIG. 27 there is shown the lancing device 10 as disposed over an area in which it is desired to express a sample of body fluid. As the force F is applied to the lancing device 10 the force F is translated through the constricting member 500 into component forces F' and F". As the force F increases, the component forces F' and F" cause the patient's skin in contact with the distal end 501 of the constricting member 500 to gather and form a pucker as shown in FIG. 28, wherein the tissue contacting surface 161 of the stimulating member 160 contacts the skin S.

In addition to forming the puckered area of skin as shown in FIG. 28, when the force F is increased on the lancing device 10, the pucker of skin is drawn into the distal end of the lancing device 10. The pucker of skin is received by the tissue contacting surface 161 of the stimulating member 160, wherein the stimulating member may include a plurality of ridges to increase frictional contact between the skin and the tissue contacting surface 161 of the stimulating member 160. In addition to forming the pucker of skin, a second force F'" is applied to the lance 42, thereby driving the distal tip of a lance or needle into the pucker of skin to form an incision therein as shown in FIG. 28.

The forces F' and F" which the constricting member 500 applies to the skin cause the skin to form the pucker as described above. Additionally, the forces F' and F" cause body fluid to pool within the pucker because the forces constrict or tourniquet vessels under the surface of the skin thereby restricting the flow of body fluid from these areas. Thus, by constricting the flow of body fluid within the pucker a larger body fluid sample may be obtained from the incision formed by the lance or needle.

Figure 29:
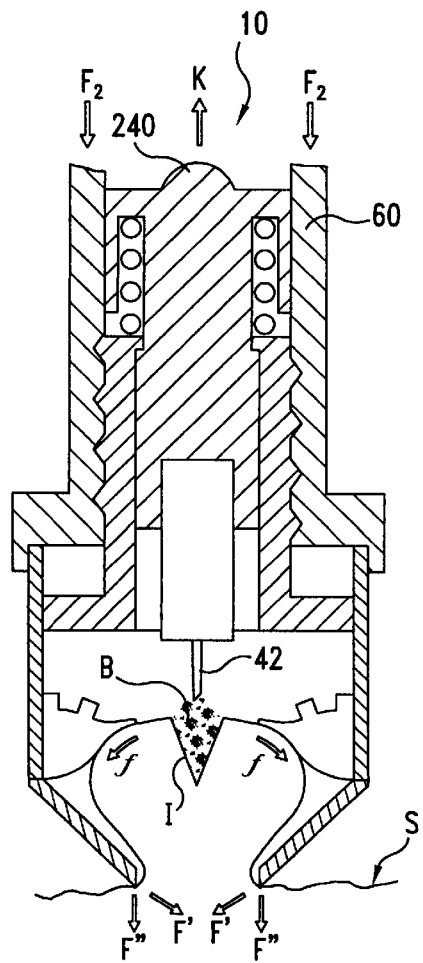
FIG. 29 is a partial cross-sectional side view illustrating the lancing action and spreading of the formed incision by the stimulating member.

Referring now to FIG. 29 there is shown the lancing device 10 wherein the lance or needle 42 has been retracted by spring force K after an incision I has been formed in the patient's skin. As shown in FIG. 29 as a greater force $F_2$ is applied to the lancing device 10, this causes the constricting member 500 to further pinch the skin in addition to causing the incision to be spread by the stimulating member 160 due to a friction force f between the skin S and the tissue contacting surface 161 of the stimulating member 160.

As a result of the stretching of the incision I, a greater amount of bodily fluid may be expressed from the incision I. Because a greater amount of body fluid may be expressed from the incision I, the lancet device may not require a repeated motion as described above in order to express a sufficiently sized sample of body fluid. Though not shown in FIGS. 27–29, the lancing device 10 may include additional stimulating means such as heat, vibration, ultrasound or other similar known methods or devices which are utilized to increase body fluid flow within a localized area.

Figure 30:
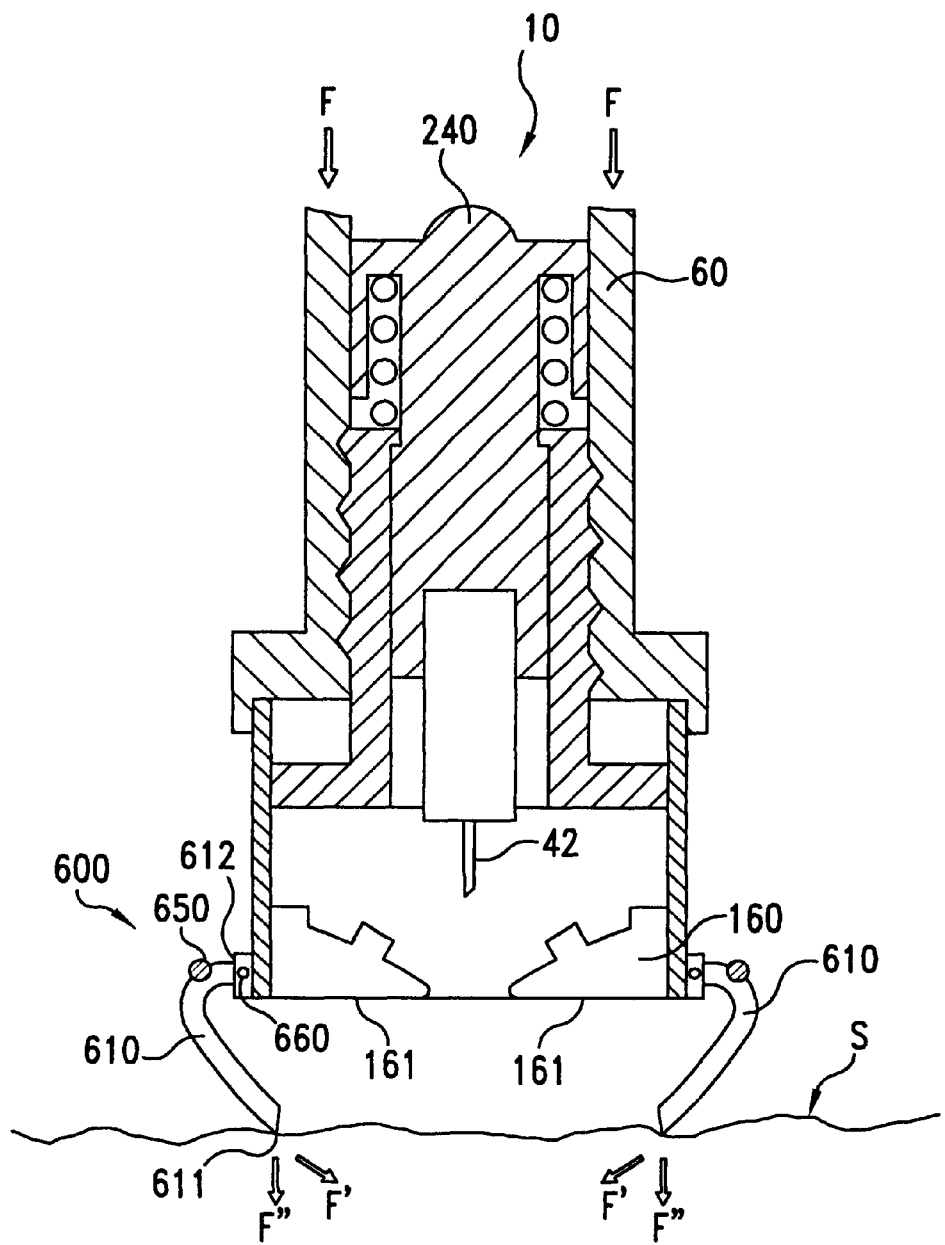
FIG. 30 is a partial cross-sectional side view of an alternative embodiment of a lancing device including a stimulating member and a constricting member.
Figure 31:
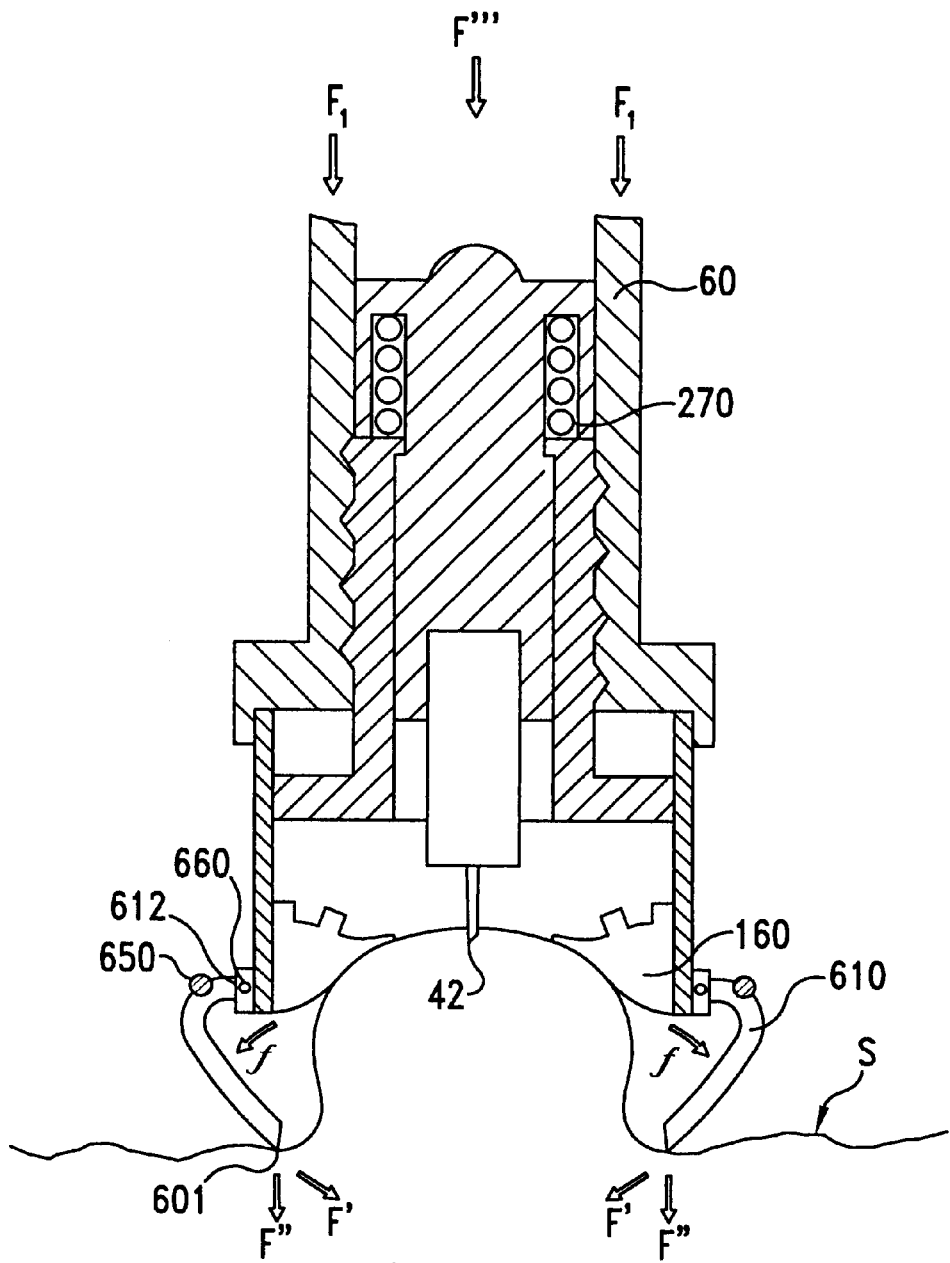
FIG. 31 is a partial cross-sectional side view of the lancing device of FIG. 30 illustrating the formation of an incision within a bulge of tissue.
Figure 32:
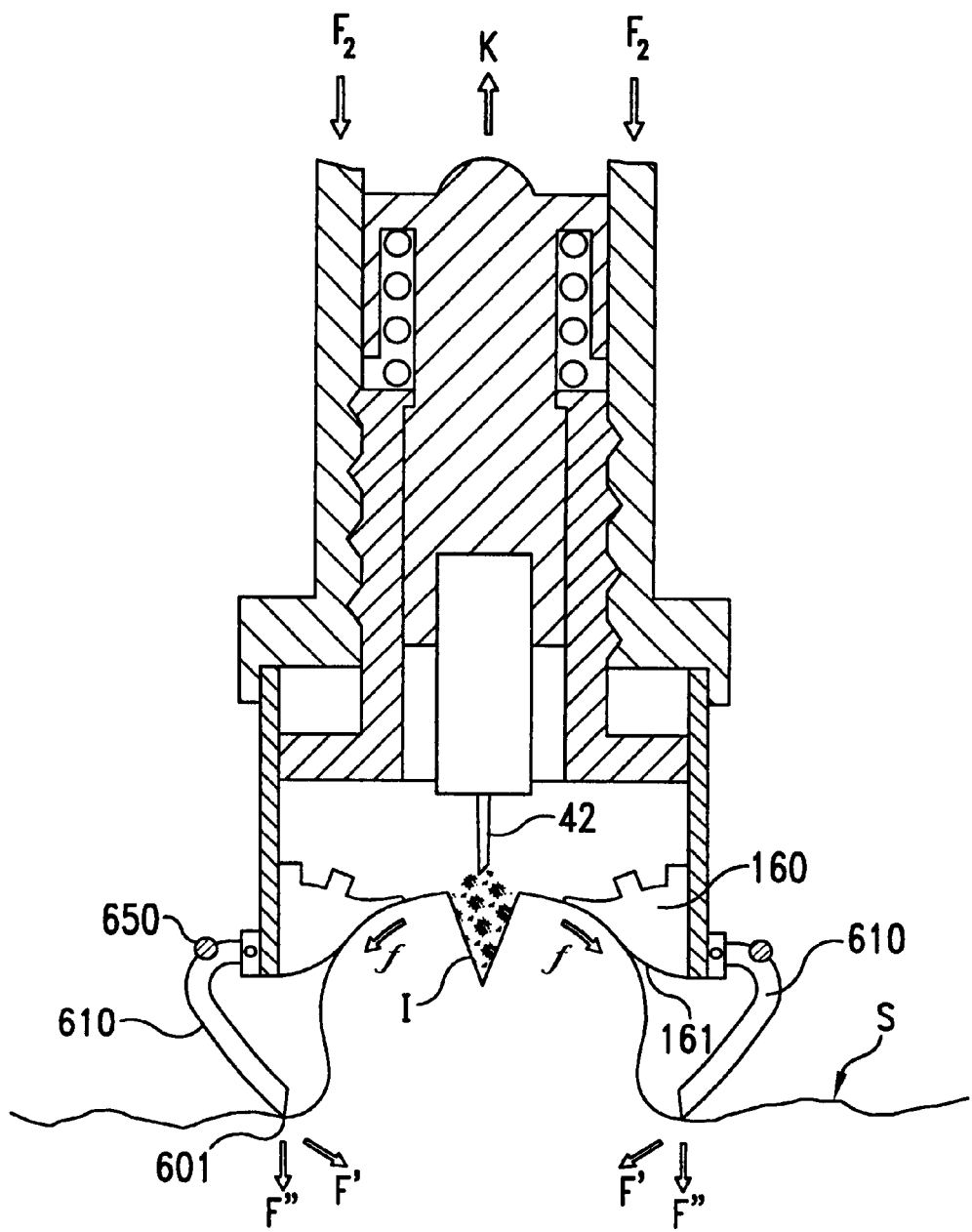
FIG. 32 is a partial cross-sectional side view of the lancing device of FIG. 31 illustrating the spreading of the incision by the stimulating member.

Referring now to FIGS. 30–32 there is shown an alternative embodiment of a constricting member 600. Wherein the constricting device 600 may be disposed about the sleeve 180 of the lancing device 10 and adjacent the distal end 181 to the sleeve 180. The constricting device 600 includes a plurality of arms 610 having a distal end 611 and a proximal end 612, a biasing member 650 and a pivot 660.

In accordance with the present invention, the proximal end 612 of the arm 610 may be pivotally attached to the sleeve 180. The arm 610 may be pivotally attached to the sleeve through a pin and block configuration as shown in FIGS. 30–32 or alternatively the proximal end 612 may be integrally formed with the sleeve 180 and pivot through the use of a live hinge or similar arrangement.

As described above the constricting device member 600 includes a biasing member 650. The biasing member 650 acts on the arms 610 thereby directing the distal tips 611 of the arms 610 to contact the skin S as shown and to provide forces F' and F".

Referring now to FIGS. 31 and 32 there is shown the lancing device 10 in use. The constricting member 600 acts upon the patient's skin to form a pucker of skin which is received within the distal end of the lancing device 10. It shall be noted that the constricting member 600 acts upon the patient's skin in the same manner as the constricting device 500 as described above with reference to FIGS. 26 through 29. Wherein the constricting device 600 and stimulating member 160 act in conjunction with one another to express a greater amount of body fluid from an incision formed in the patient's skin.

The lancing device in accordance with the present invention may be best utilized in areas where it is difficult to obtain a sufficient sample size, such as a forearm, though it is desirable to lance within this area because of the reduction in pain associated with the lancing.

Figure 33:
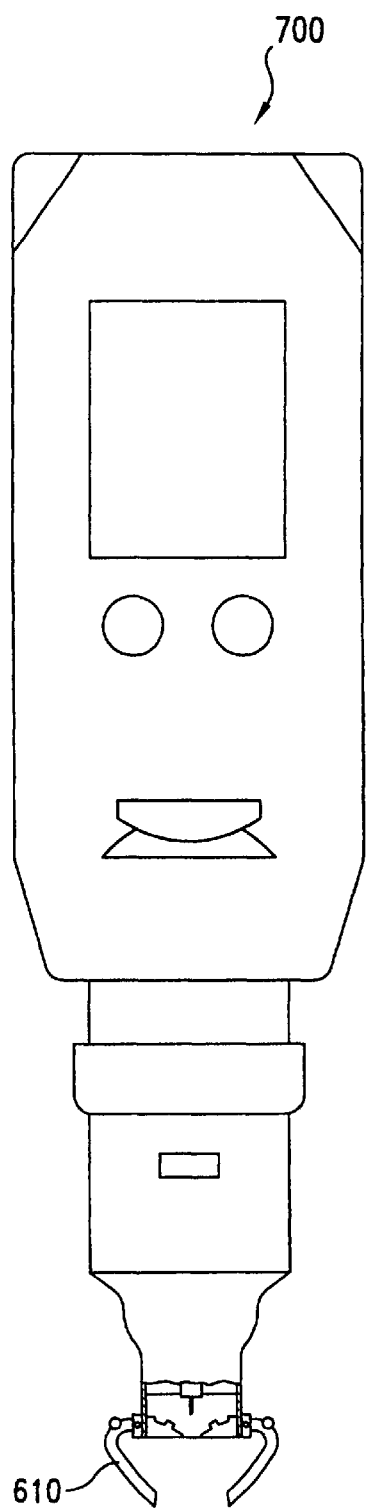
FIG. 33 is a side view illustrating a glucose monitoring device in accordance with the present invention.

Referring now to FIG. 33, there is shown a further alternative embodiment of a lancing device 700 in accordance with the present invention, wherein the lancing device 700 further includes a body fluid sampling and testing device. The lancing device 700 may be utilized upon a patient's forearm or similar area, wherein the stimulating member and constricting member in conjunction with a needle or lancet produce a sample size of sufficient volume wherein a test may be performed thereon. For example, the lancing device 700 may be that which is shown and described in co-pending U.S. Provisional Patent Application No. 60/296,950 filed Jun. 8, 2001, now abandoned, Attorney Dkt. No. 018176-385 and to co-pending U.S. Provisional Patent Application No. 60/297,098 filed Jun. 8, 2001, now abandoned, Attorney Dkt. No. 018176-382, the entirety of which are hereby incorporated by reference.

It will be appreciated that the present invention enables a sampling of blood or interstitial fluid to be taken from areas of the body, such as a forearm, that are less insensitive to pain, despite the fact that those areas typically have relatively less fluid as compared, for example, to fingertips (which are highly sensitive to pain).

Therefore, there will be less reluctance on the part of users to have a sampling procedure performed. For example, diabetics who experience a relatively high fear of pain will be less likely to neglect monitoring their blood glucose levels.

In lieu of using a lancet as a skin-lancing medium, other skin-lancing media can be used, such as a laser, or known pneumatic or hydraulic injectors of the type which inject pressurized gas or liquid against the skin. Such auto injectors are sold by Becton-Dickinson, for example, to inject insulin. By eliminating the insulin and merely injecting the gas (e.g., air or nitrogen) or liquid (e.g., water) at pressures above 30 psi. an incision could be formed in the skin for taking samples of body fluid. Advantageously, small particles could be mixed with the gas to promote the tissue-cutting action. The particles could comprise carbon particles of from 1 micron to 0.010 inches in diameter.

In addition to that which is described above, it is contemplated that the lance or needle may remain within the incision during the collection of the sample. Additionally a force may be applied to the lance or needle to stimulate fluid flow from the incision, for example the lance or needle may be vibrated to express fluid from the incision. It shall be understood that the terms "remain within the incision" shall mean to include the instances where the lance or needle remains in contact with the patient's tissue inside of the incision, or where the lance or needle is withdrawn just distal the incision though remains in fluid contact with the body fluid expressed from the incision.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims. In addition, each of the methods and apparatuses described herein may be utilized with testing systems and devices such as those which are contained within the co-filed U.S. patent application having Ser. No. 60/297,187 filed Jun. 8, 2001, now abandoned, entitled "Control Solution Packet and Methods of Use for Bodily Fluid Sampling Devices;" U.S. patent application having Ser. No. 60/296,950 filed Jun. 8, 2001, now abandoned, entitled "Lancet Device Having Capillary Action;" U.S. patent application having Ser. No. 60/297,045 filed Jun. 8, 2001, now abandoned, entitled "Method of Sampling Interstitial Fluid for Glucose Monitoring;" U.S. patent application having Ser. No. 60/296,989 filed Jun. 8, 2001, now abandoned, entitled "Cassette for a Glucose Monitoring System;" and U.S. patent application having Ser. No. 60/296,949 filed Jun. 8, 2001, now abandoned, entitled "Test Media for Glucose Monitoring Systems;" the entirety of which are herein incorporated by reference.

What is claimed:

1. A device for sampling body fluid comprising:
a housing having an open end;
a skin-lancing mechanism mounted in the housing for applying a skin-lancing medium against a skin surface to form an incision therein, and then removing the skin-lancing medium from the incision;
a constricting member mounted to the housing at the open end thereof for movement relative to the housing, the constricting member radially disposed about a longitudinal axis of the housing and pivotally attached thereto, wherein the constricting member causes the skin surface to form a bulge in response to a pressing on the housing; and
a stimulator member mounted to the housing at the open end thereof for movement relative to the housing, the stimulator member extending about the longitudinal axis of the housing and having an end face adapted to engage the skin surface of the bulge and to stretch open the incision in response to a pressing of the end face against the skin surface.

2. The device according to claim 1 wherein the end face is inclined to generally face the axis.

3. The device according to claim 1 wherein the stimulator member extends continuously about the axis.

4. The device according to claim 1 wherein the stimulator member includes circumferentially spaced interruptions.

5. The device according to claim 1 wherein the stimulator member is movable relative to the housing along the axis.

6. The device according to claim 5, wherein the stimulator member and the constricting member are movable relative to the housing and are interconnected to move axially in mutually opposite directions.

7. The device according to claim 1 wherein the stimulator member comprises a first stimulator member, and further including at least one additional stimulator member arranged in telescoping relationship to the first stimulator member, the stimulator members being relatively movable along the axis.

8. The device according to claim 7 wherein the stimulator members include first and second stimulator members which are movable relative to the housing and are interconnected to move axially in mutually opposite directions.

9. The device according to claim 6 wherein the first and second stimulator members are interconnected by levers, each lever having opposite ends, each lever being pivoted intermediate the ends of each lever for rotation about an axis extending orthogonally relative to the longitudinal axis of the housing.

10. The device according to claim 1 wherein the stimulator member comprises a helical spring.

11. The device according to claim 1 further including a second stimulator chosen from the group consisting of a heating mechanism for heating the stimulator member or constricting member; and a vibrator mechanism for vibrating the stimulator member or constricting member.

12. A device for sampling body fluid comprising:
a housing having an open end;
a skin-lancing mechanism mounted in the housing for applying a skin-lancing medium against a skin surface to form an incision therein, and then removing the skin-lancing medium from the incision;
a constricting member mounted to the housing at the open end thereof for movement relative to the housing, the constricting member radially disposed about a longitudinal axis of the housing and pivotally attached thereto, wherein the constricting member causes the skin surface to form a bulge in response to a pressing on the housing;
a stimulator member mounted to the housing at the open end thereof for movement relative to the housing, the stimulator member extending about the longitudinal axis of the housing and having an end face adapted to engage the skin surface of the bulge and to stretch open the incision in response to a pressing of the end face against the skin surface; and
wherein the constricting member comprises at least two legs pivotally mounted to the housing, and biasing members for biasing the legs in response to a force applied to the housing.

13. A body fluid sampling device, comprising:
a housing;
a skin-lancing mechanism coupled to the housing and adapted to form an incision in skin; and
a stimulator member coupled to the housing, the stimulator member including a flexible membrane with a skin contacting surface for frictionally engaging the skin to stretch open the incision upon pressing the stimulator member against the skin.

14. The device of claim 13, wherein the skin contacting surface has a plurality of rings radially disposed about an aperture in the flexible membrane.

15. The device of claim 13, wherein the stimulator member includes a raised member disposed upon the skin contacting surface in a spiraling manner for directing fluid into the incision.

16. A body fluid sampling device, comprising:
a housing;
a skin-lancing mechanism coupled to the housing and adapted to form an incision in skin;
a stimulator member coupled to the housing, the stimulator member including a flexible membrane with a skin contacting surface for frictionally engaging the skin to stretch open the incision upon pressing the stimulator member against the skin; and
a constricting member coupled to the stimulator member for puckering the skin against the stimulator member upon pressing the constricting member against the skin.

17. The device of claim 16, wherein the constricting member is constructed of pliable material for flexing the constricting member to pucker the skin upon pressing the constricting member against the skin.

18. The device of claim 16, wherein the constricting member includes a plurality of arms pivotally coupled to the stimulator member to pucker the skin.

19. The device of claim 18, wherein each of the arms has a biasing member for biasing each of the arms against the skin.

20. The device of claim 16, wherein the skin contacting surface has a plurality of rings radially disposed about an aperture in the flexible membrane.

21. The device of claim 16, wherein the stimulator member includes a raised member disposed upon the skin contacting surface in a spiraling manner for directing fluid into the incision.

22. A body fluid sampling device, comprising:
a housing;
a skin-lancing mechanism coupled to the housing and adapted to form an incision in skin;

a constricting member coupled to the housing to pucker the skin upon pressing the constricting member against the skin; and wherein the constricting member includes a plurality of arms pivotally coupled to the housing to pucker the skin.

23. The device of claim 22, wherein each of the arms has a biasing member for biasing each of the arms against the skin.

24. The device of claim 22, further comprising a stimulator member coupled between the housing and the constricting member, the stimulator member including a skin contacting surface for frictionally engaging the skin to stretch open the incision upon pressing the stimulator member against the skin.

25. A method of obtaining a sample of body fluid from a body, comprising the steps of:

A) applying a skin-lancing device against the skin of a user to form an incision in the skin;

B) removing the skin-lancing device from the incision; and thereafter

C) applying a force to depress the skin in a manner forming a ring of depressed body tissue in surrounding relationship to the incision wherein a stimulating member stretches the incision open, whereby body fluid is expressed from the opening of the incision; and wherein step C comprises applying the force progressively closer to the incision.

26. The method according to claim 25, wherein a force between the stimulating member and the skin causes the stimulating member to retain the skin in a stretched position.

27. The method according to claim 25, wherein step C includes applying the force in a direction inclined generally toward the incision.

28. The method according to claim 25, wherein step C includes applying heat in a region of the incision.

29. The method according to claim 25, wherein step C includes applying ultrasonic frequency to a region of the incision.

30. The method according to claim 25, wherein step A comprises lancing a region of the body of the user other than a finger tip.

31. The method according to claim 25, wherein step A comprises applying a lancet against the skin.

* * * * *